US009340488B2

(12) United States Patent
Dagan et al.

(10) Patent No.: US 9,340,488 B2
(45) Date of Patent: May 17, 2016

(54) SYNTHETIC ANALOGS OF SPHINGOLIPIDS

(71) Applicants: HADASIT MEDICAL RESEARCH SERVICES & DEVELOPMENT LIMITED, Jerusalem (IL); YISSUM RESEARCH DEVELOPMENT COMPANY OF THE HEBREW UNIVERSITY OF JERUSALEM LTD., Jerusalem (IL)

(72) Inventors: Arie Dagan, Jerusalem (IL); Shimon Slavin, Tel Aviv (IL); Shimon Gatt, Jerusalem (IL); Jeremy Zahavy, Modiin (IL)

(73) Assignees: HADASIT MEDICAL RESEARCH SERVICES & DEVELOPMENT LIMITED, Jerusalem (IL); YISSUM RESEARCH DEVELOPMENT COMPANY OF THE HEBREW UNIVERSITY OF JERUSALEM LTD., Jerusalem (IL)

(*) Notice: Subject to any disclaimer, the term of this patent is extended or adjusted under 35 U.S.C. 154(b) by 0 days.

(21) Appl. No.: 14/540,621

(22) Filed: Nov. 13, 2014

(65) Prior Publication Data

US 2015/0073003 A1   Mar. 12, 2015

Related U.S. Application Data

(62) Division of application No. 12/742,045, filed as application No. PCT/IL2008/001472 on Nov. 9, 2008, now Pat. No. 8,962,891.

(30) Foreign Application Priority Data

Nov. 8, 2007   (IL) .......................... 187247

(51) Int. Cl.
| A61K 31/133 | (2006.01) |
| C07C 215/12 | (2006.01) |
| C07C 215/10 | (2006.01) |
| A61K 31/4745 | (2006.01) |
| A61K 31/513 | (2006.01) |

(52) U.S. Cl.
CPC ............ *C07C 215/12* (2013.01); *A61K 31/133* (2013.01); *A61K 31/4745* (2013.01); *A61K 31/513* (2013.01); *C07C 215/10* (2013.01)

(58) Field of Classification Search
CPC   A61K 31/513; A61K 31/133; A61K 31/4745
See application file for complete search history.

(56) References Cited

U.S. PATENT DOCUMENTS

| 2,363,082 A | 11/1944 | Ringk |
| 2,877,245 A | 3/1959 | Vincent |
| 3,324,043 A | 6/1967 | Krum |
| 3,432,603 A | 3/1969 | Zenitz |
| 4,331,685 A | 5/1982 | Tokuda et al. |
| 4,742,058 A | 5/1988 | Yamatsu et al. |
| 5,068,120 A | 11/1991 | Yarger et al. |
| 5,075,482 A | 12/1991 | Seltzer et al. |
| 5,132,426 A | 7/1992 | Seltzer et al. |
| 5,583,088 A | 12/1996 | Kawamura |
| 5,604,229 A | 2/1997 | Fujita et al. |
| 5,990,170 A | 11/1999 | Della Valle et al. |
| 6,410,597 B1 * | 6/2002 | Bieberich ............... A61K 31/16 514/613 |
| 7,323,462 B2 | 1/2008 | Allerton et al. |
| 2005/0075397 A1 | 4/2005 | Msika et al. |
| 2005/0267096 A1 | 12/2005 | Allerton et al. |
| 2006/0014280 A1 | 1/2006 | Condie et al. |
| 2011/0028719 A1 * | 2/2011 | Slon-Usakiewicz ....... G01N 33/6896 544/177 |

FOREIGN PATENT DOCUMENTS

| EP | 0 627 406 A1 | 12/1994 |
| GB | 1 018 989 A | 2/1966 |
| JP | H04-244092 A | 9/1992 |
| JP | H06-009512 A | 1/1994 |
| JP | H08-011435 A | 1/1996 |
| JP | H09-003467 A | 1/1997 |
| JP | H11-500411 A | 1/1999 |
| JP | 2005-518390 A | 6/2005 |
| WO | 94/08943 A1 | 4/1994 |
| WO | 96/18391 A2 | 6/1996 |
| WO | 01/79152 A1 | 10/2001 |
| WO | 03/027058 A1 | 4/2003 |
| WO | 03/055462 A2 | 7/2003 |
| WO | 2004/022530 A1 | 3/2004 |
| WO | 2006/116703 A2 | 11/2006 |

OTHER PUBLICATIONS

Biberich et al, Cancer Letters, 2002, 181(1), 55-64.*
Levade, et al. Biochem. Biophys. Acta 1438: 1-17 (1999).
Mathias, et al. Biochem. J. 335, 465-80 (1998).
Perry, et al. Biochem. Biophys. Acta 1436, 233-43 (1998).
Riboni, et al. Prog. Lipid Res. 36, 153-95 (1997).
Fernandis, et al. Curr. Opin. Lipidol. 18: 121-8 (2007).
Hait, et al. Biochem. Biophys. Acta 1758: 2016-26 (2006).
Hannun, et al. Biochem. Biophys. Acta 1154, 223-36 (1993).
Hannun, et al. Trends Cell Biol. 10, 73-80 (2001).
Higgins, et al. Trends Biochem. Sci. 17, 18-21 (1992).
Yang, et al. Cell. Biochem. Biophys., 40: 323-50 (2004).
Ohanian, et al. Cell. Mol. Life Sci., 58: 2053-68 (2001).

(Continued)

Primary Examiner — Shailendra Kumar
(74) Attorney, Agent, or Firm — Oliff PLC

(57) ABSTRACT

The present invention provides new ceramide analogs indicated as the compounds of formula (II). These novel analogs exhibit a significant anti cancerous effect and are therefore provided as a pharmaceutical composition for treating cell proliferative diseases, neurodegenerative disorders, metabolism-associated conditions, infectious diseases, and immune-related disorders. The invention further provides combined compositions and kits combining the novel ceramide analogs of formula (II) with an additional therapeutic agent.

4 Claims, 7 Drawing Sheets

(56) References Cited

OTHER PUBLICATIONS

Pandey, et al. Exp. Mol. Pathol., 82: 298-309 (2007).
Dagan, et al. Biochem. Biophys. Acta 1633:161-9 (2003).
Eyster K.M., Adv. Physiol. Educ., 31: 5-16 (2007).
Zheng, et al. Biochem. Biophys. Acta 1758: 1864-84 (2006).
Gomez-Munoz, Biochem. Biophys. Acta 1391, 92-109 (1998).
Stover, et al. J. Pharmacol. Exp. Ther., 307: 468-75 (2003).
Endo, et al. Cancer Research, 51, 1613-8 (1981).
Wagner, Lancet Aug. 27-Sep. 2, 2005; 266 (9487):733-41.
Jarvis, et al. Curr. Opin. Oncol., 10: 552-9 (1998).
Kolesnick, et al. Oncogene, 22: 5897-906 (2003).
Charles, et al. Cancer Chemother. Pharmacol., 47: 444-50 (2001).
Hail, et al. Apoptosis, 11: 1677-94 (2006).
Cuvillier, et al. Cell Death Differ., 8: 162-71 (2001).
Liu, et al. FASEB J., 15: 719-30 (2001).
Gouaze, et al. Mol. Cancer Ther., 3: 633-9 (2004).
Liu, et al. j. Biol. Chem., 274: 1140-6 (1999).
Cabot, et al. FEBS Lett. 394, 129-131 (1996).
Cabot, et al. FEBS Lett. 431, 185-99 (1998).
Lavie, et al. J. Biol. Chem., 272, 1682-7 (1997).
Lucci, et al. Cancer 86, 300-311 (1999).
Nicholson, et al. Br. J. Cancer, 81, 423-30 (1999).
Scarlatti, et al. FASEB J. 71, 2239-2341 (2003).
Gewirtz, et al. Breast Cancer Res. and Treatment 62, 223-235 (2000).
Struckhoff, et al. J. Pharm. Exp. Ther. 309, 523-532 (2004).
Reynolds, et al. Cancer Letters 206, 169-180 (2004).
Bair, et al. Journal of Medicinal Chemistry, 1991, 34 (7), 1983-90.
Labaied, et al. Malaria Journal, 2004, 3:49, p. 1-10.
Aug. 16, 2012 Office Action issued in U.S. Appl. No. 12/742,045.
Apr. 1, 2013 Office Action issued in U.S. Appl. No. 12/742,045.
Sep. 9, 2013 Office Action issued in U.S. Appl. No. 12/742,045.
Mar. 31, 2014 Office Action issued in U.S. Appl. No. 12/742,045.
Oct. 16, 2014 Notice of Allowance issued in U.S. Appl. No. 12/742,045.
Carter et al., Chemotherapy of Cancer, second edition, John Wiley & Sons, N.Y., N.Y., 1981, pp. 362-365.
Ogura et al, Biochem. et Biophysic. Acta, 1483(2000), 111-118.
Avora et al, J. Lipid Research, vol. 13, 1972, 86-91.
Overloop et al, J. Lipid Research, vol. 47, 2006, 268-283.
Lambert et al, J. Org. Chem., 29(10), 3116-3118, 1964.
Scott et al, Tetrahedron Letters., 1999, 40(42), 7581-7584.

\* cited by examiner

SYNTHETIC ANALOGS OF SPHINGOLIPIDS

This application is a DIV of Ser. No. 12/742,045, filed on Oct. 25, 2010, now U.S. Pat. No. 8,962,891, which is a 371 of PCT/IL08/01472, filed on Nov. 11, 2008.

FIELD OF THE INVENTION

The present invention relates to novel compounds, particularly suitable in the manufacture of medicaments for treating proliferative and degenerative diseases, as well as infectious and metabolic diseases.

BACKGROUND OF THE INVENTION

During the past decade there was an enormous increase in research on sphingolipids due to discoveries that implicated members of this group in signal transduction processes [reviewed in Levade et al., *Biochim. Biophys. Acta* 1438, 1-17 (1999); Mathias et al., *Biochem. J.* 335, 465-80 (1998); Perry et al., *Biochim. Biophys. Acta* 1436, 283-43 (1998); Riboni et al., *Prog. Lipid Res.* 36, 153-95 (1997); and Fernandis et al. *Curr. Opin. Lipidol.* 18: 121-8 (2007)]. The most studied compound was ceramide, and more recently sphingosine phosphate [Hait et al., *Biochim. Biophys. Acta,* 1758: 2016-26 (2006)]. Ceramicle was shown to play a role in the regulation of key processes such as growth inhibition, differentiation and apoptosis [Hannun et al., *Biochim. Biophys. Acta* 1154, 223-36; Hannun et al., *Trends Cell Biol.* 10, 78-80 (2001); Higgins et al., *Trends Biochem. Sci.* 17, 18-21 (1992); and Yang et al., *Cell Biochem. Biophys.,* 40: 823-50 (2004)].

Sphingomyelin (SPM) is generally considered as the primary metabolic source of ceramide, whose generation in particular locations in the cell makes it suitable for mediating cellular signaling processes. An increased de novo synthesis of ceramide has also been described as a potential source for signaling [Ohanian et al., *Cell. Mol. Life Sci.,* 58: 2053-68 (2001); and Pandey et al., *Exp. Mol. Pathol.,* 82: 298-309 (2007)]. Therefore, a major effort has been directed to modulate the generation of intracellular ceramide by sphingomyelinases, mostly the neutral membrane-bound enzyme, although the acidic enzyme has also been implicated. However, it should be emphasized that modification of the biosynthetic mechanisms such as reduction of the conversion of ceramide to SPM or glycolipids and, in parallel, decreasing its hydrolysis by ceramidases would also increase its concentration in the cell [Dagan et al., *Biochim. Biophys. Acta.,* 1633:161-9 (2003)].

The role of sphingolipids in signal transduction [reviewed in Eyster K. M., *Adv. Physiol. Educ.,* 31: 5-16 (2007); Zheng et al., *Biochim. Biophys. Acta.* 1758: 1864-84 (2006); Riboni et al., *Prog. Lipid Res.* 36, 153-95 (1997); and Gomez-Munoz, *Biochim. Biophys. Acta* 1391, 32409 (1998)] have been extensively studied, and were proposed to operate through the "sphingomyelin cycle". According to this hypothesis, binding a particular extracellular ligand to its receptor activates a plasma membrane-bound sphingomyelinase, giving rise to ceramide, which acts as a mediator of the intracellular effects of the ligand. Numerous publications describe and emphasize the role of ceramide in cell killing by apoptosis, as well as its effect on important cellular events such as proliferation, differentiation and reaction to stress conditions. Of particular interest are also reports that short chain, cell-permeable (e.g., $C_2$ or $C_6$) ceramides evoke biological responses that lead to cell killing [Stover et al., *J. Pharmacol. Exp. Ther.,* 307: 468-75 (2003)]. Other studies, using the precursor of ceramide, sphingosine, have shown its effects on the cell growth and viability. Furthermore, sphingosine was shown to inhibit protein kinase C and to increase the intracellular concentration of calcium ions. The phosphorylated form of sphingosine, sphingosine-1-phosphate, has been shown to be a potent activator of phospholipase D; di- or tri-methylated sphingosine was shown to inhibit growth of cancer cells [Endo et al., *Cancer Research,* 51, 1613-8 (1981)].

WO 03/027058 relates to a group of compounds suitable for the treatment of parasitic diseases and cancerous diseases for killing of wild type and drug-resistant cancer cells, particularly by inhibiting the synthesis of sphingolipids and ceramides. The compounds disclosed in WO 03/027058 essentially have an alkyl backbone substituted with an alkyl or alkenyl chain which itself may be substituted.

It has now surprisingly been found that the compounds of WO 03/027058 are also effective against immuno-degenerative disorders, in particular against GVHD (Graft Versus Host Disease). GVHD is a type of incompatibility reaction of transplanted cells against host tissues that possess an antigen not possessed by the donor. It is a common complication of allogeneic bone marrow transplantation. After bone marrow transplantation, T cells present in the graft, either as contaminants or intentionally introduced into the host, attack the tissues of the transplant recipient after perceiving host tissues as antigenically foreign. A wide range of host antigens can initiate GVHD, among them the HLAs. However, GVHD can occur even when HLA-identical siblings are the donors. HLA-identical siblings or HLA-identical unrelated donors (called a minor mismatch as opposed to differences in the HLA antigens, which constitute a major mismatch) often still have genetically different proteins that can be presented on the MHC.

Clinically, GVHD is divided into acute and chronic forms. The acute or fulminant form of the disease is observed within the first 100 days post, transplant, and the chronic form of GVHD is defined as that which occurs after 100 days. This distinction is not arbitrary: acute and chronic GVHD appear to involve different immune cell subsets, different cytokine profiles, and different types of target organ damage.

Classically, acute GVHD is characterized by selective damage to the liver, skin and mucosa, and the gastrointestinal tract. Newer research indicates that other GVHD target organs include the immune system itself (the hematopoietic system, e.g. the bone marrow and the thymus), and the lungs in the forth of idiopathic pneumonitis. Chronic GVHD damages the above organs, but also causes changes to the connective tissue (e.g. of the skin and exocrine glands).

GVHD can largely be avoided by performing a T-cell depleted bone marrow transplant. These types of transplants result in reduced target organ damage and generally less GVHD, but at a cost of diminished graft-versus-tumor effect, a greater risk of engraftment failure, and general immunodeficiency, resulting in a patient more susceptible to viral, bacterial, and fungal infection.

Methotrexate and cyclosporin are common drugs used for GVHD prophylaxis. In a multi-center study [*Lancet* 2005 Aug. 27-Sep. 2; 366 (9487):733-41], disease-free survival at 3 years was not different between T cell depleted and T cell replete transplants.

While donor T-cells are undesirable as effector cells of GVHD, they are valuable for engraftment by preventing the recipient's residual immune system from rejecting the boric marrow graft (host-versus-graft). Additionally, as bone marrow transplantation is frequently used to cure malignant disorders (most prominently the leukemias), donor T-cells have proven to have a valuable graft-versus-tumor effect. A great deal of current research on allogeneic bone marrow transplantation involves attempts to separate the undesirable GVHD aspects of T-cell physiology from the desirable graft-versus-tumor effect.

A key function of the immune system is the control of self-reactivity. Under normal circumstances, the immune system is unresponsive to self-antigens. However, when the immune balance is perturbed, self-reactive lymphocytes may cause autoimmune diseases. Different diseases may develop, depending on the targets of sensitized T cells and antibodies reacting against self-antigens. Thus, lymphocytes reacting against encephalitogenic determinants of the central nervous system typically cause multiple sclerosis (MS), whereas lymphocytes reacting against pancreatic islets typically cause type 1 insulin dependent diabetes mellitus (IDDM). Other autoimmune diseases may be mediated primarily by antibodies such as autoimmune hemolytic anemia, while other autoimmune syndromes may result in multi-organ or systemic disease, such as systemic lupus erythematosus (SLE).

As for the involvement of ceramide and sphingolipid metabolism in cancer, pertinent to this are two lines of study: The first demonstrated that apoptosis induced by administration of a variety of chemotherapeutic agents is mediated by ceramide [Jarvis et al., *Curr. Opin. Oncol.*, 10: 552-9 (1998); Kolesnick et al., *Oncogene*, 22: 5897-906 (2003); Charles et al., *Cancer Chemother. Pharmacol.*, 47: 444-50 (2001); and Hail et al., *Apoptosis*, 11: 1677-94 (2006)]. Anthracyclins (e.g., daunorubicin) have been shown to induce ceramide accumulation which subsequently led to death of cancer cells [Cuvillier et al., *Cell Death Differ.*, 8: 162-71 (2001)]. The second line of study showed that drug-resistant cancer cells differ in their sphingolipid metabolism from drug-sensitive ones. Of special interest in this respect are the studies of Cabot [Liu et al., *FASEB J.*, 15: 719-30 (2001) and Gouaze et al., *Mol. Cancer Ther.*, 3: 633-9 (2004)] which demonstrate that glucosylceramide, a direct metabolic product of ceramide, is elevated in several drug-resistant cells overexpressing the P-glycoprotein pump (Pgp). Overexpression of glucosylceramide synthetase (GCS), which synthesizes said glycolipid, by a retroviral expression system, results in conversion of doxorubicin-sensitive cells into resistant ones [Liu et al., *J. Biol. Chem.*, 274: 1140-6 (1999)]. Conversely, inhibition of GCS expression, by antisense technology, results in increased sensitivity to doxorubicin. Cabot also suggests that drug-resistance modulators, such as tamoxifen, verapamil, and cyclosporine analog PSC 833 exert their effect by inhibition of GCS [Cabot et al., *FEBS Lett.* 394, 129-131 (1996); Cabot et al., *FEBS Lett.* 431, 185-99 (1998); Lavie et al., *J. Biol. Chem.*, 272, 1682-7 (1997); and Lucci et al., *Cancer* 86, 300-311 (1999)] resulting in an increase of cellular ceramide. Accordingly, Nicholson [Nicholson et al., *Br. J. Cancer*, 81, 423-30 (1999)] shows that the GCS inhibitor, 1-phenyl-2-decanoylamino-3-morpholino-1-propanol, killed preferentially multidrug-resistant cells, compared to their drug-sensitive counterparts. Taken together, the above studies suggest a metabolic mechanism, which in MDR-cells decreases their ceramide content by converting it to glucosylceramide, making them resistant to a series of chemotherapeutic drugs. As for the relationship between ceramide induction of apoptosis and death to breast cancer, a few recent publications [Scarlatti et al., *FASEB J.* 71, 2239-2341 (2003); Gewirtz et al., *Breast Cancer Res. and Treatment* 62, 223-235 (2000); and Struckhoff et al., *J. Pharm. Exp. Ther.* 309, 523-532 (2004)] and the review by Reynolds, Mauer and Kolesnick [Reynolds et al., *Cancer Letters* 206, 169-180 (2004)] summarize the relationship between these three elements and discuss the potential effect of pharmacological manipulation of sphingolipids metabolism to enhance tumor cell ceramide. Interest in the involvement of ceramide in signaling processes is emphasized by the appearance of thousands of articles and hundreds of reviews on this aspect. However, in view of the crucial role of sphingolipids in many pathologies, need is felt for novel sphingolipid analogs for use as therapeutic agents.

No effective therapy exists against any of the autoimmune diseases, nor is the etiology of either one of the above well understood. However, the feasibility to down-regulate anti-self reactivity may provide an option for cure, regardless of the etiology of each particular autoimmune disease.

In the absence of specific treatment for autoimmune diseases, treatment of patients with active disease is based on symptomatic therapy. Self-reactive lymphocytes cause an uncontrolled inflammatory reaction that is propagated by a cascade of secondary responses. Current medications are used either to control this inflammation, or, in more serious cases, to eliminate or control self-reactive lymphocytes using immunosuppressive agents. However, the immunosuppressive treatment is generally not very effective and is certainly not curative. In addition, long-term consumption of immunosuppressive agents (e.g. corticosteroids; cyclophosphamide; imuran, or cyclosporin A) is frequently associated with severe and occasionally fatal outcomes. These may be due to side effects associated with these drugs, or to the consequences of effective immunosuppression, including infections and secondary malignancy. Therefore, the available modalities are far from being satisfactory in treating autoimmune diseases, particularly not progressive and life-threatening ones such as MS, IDDM or SLE.

It is therefore an object of this invention to provide novel compounds which are in particular suitable for treating proliferative disorders.

It is another object of the present invention to provide novel compounds, and combination of compounds, optionally with a further therapeutic agent, which are suitable in treating infections, metabolic disorders, and degenerative diseases.

Other objects and advantages of the present invention will appear as description proceeds.

SUMMARY OF THE INVENTION

A first aspect of the invention relates to a compound of formula (II), being:

wherein
X represents a hydrogen atom or OH;
Y represents

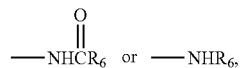

wherein $R_6$ represents a $C_{2-20}$ linear or branched alkyl or alkenyl chain which may be optionally substituted with hydroxyl; and W represents a hydrogen atom or $C_{1-20}$ linear or branched alkyl or alkenyl chain which may be optionally substituted with hydroxyl, or a pharmaceutically acceptable salt or isomer thereof.

According to a specific embodiment, the compound of formula (II) may be selected from:

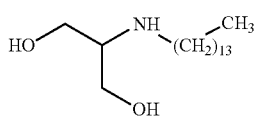

designated herein as AD2750;

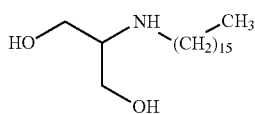

designated herein as ADYZ252;

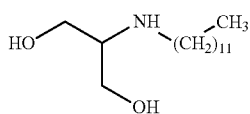

designated herein as ADYZ74;

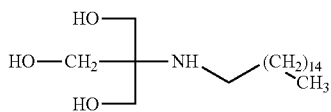

designated herein as ADYZ243;

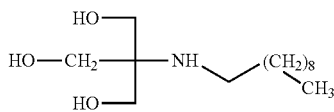

designated herein as ADYZ195;

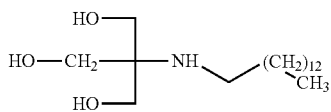

designated herein ADYZ196; and

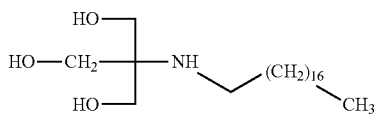

designated herein ADYZ197.

According to another aspect, the invention relates to a pharmaceutical composition comprising a compound of formula (II) as defined by the invention or any pharmaceutically acceptable salt or isomer thereof. The composition of the invention may optionally further comprise at least one pharmaceutically acceptable carrier, diluent, excipient and/or additive.

According to a particular embodiment, the compositions of the invention may specifically be applicable for the treatment of a pathological disorder selected from the group consisting of proliferative disorders, neurodegenerative disorders, metabolism-associated conditions, infectious diseases, and immune-related disorders.

In yet another aspect, the invention provides a composition comprising a combination of at least one compound of formula (II) or a pharmaceutically acceptable salt or isomer thereof, and at least one additional therapeutic agent, optionally further comprising at least one pharmaceutically acceptable carrier, diluent, excipient and/or additive.

According to one embodiment the additional therapeutic agent may be selected from topoisomerase inhibitors, nucleic acids antimetabolites, and antimitotic agents.

Still further, the invention provides a kit for providing a therapeutic effect in a subject in need thereof comprising:
(a) at least one compound of formula (II) or a pharmaceutically acceptable salt or isomer or other derivative thereof, or any combination or mixture thereof, and a pharmaceutically acceptable carrier or diluent, optionally, in a first unit dosage form; (b) at least one therapeutic agent selected from topoisomerase inhibitors, nucleic acids antimetabolites, and antimitotic agents and a pharmaceutically acceptable carrier or diluent, optionally, in a second unit dosage form; (c) container means for containing said first and second dosage forms; and (d) instructions for use.

The invention further provides a method for the treatment of a subject suffering from a pathological disorder comprising the step of administering to said subject a therapeutically effective amount of the compound of Formula II or any composition, combined composition or kit thereof. According to a particular embodiment, the method of the invention may be applicable for treating a disorder being any one of a proliferative disorder, immune-related disorder, neurodegenerative disorder, infectious disease and metabolism-associated condition.

According to another aspect, the invention provides the use of a compound of formula (I), or a salt or isomer thereof, in the preparation of a medicament for treating a pathologic disorder selected from the group consisting of proliferative disorders, neurodegenerative disorders, metabolism-associated conditions, infectious diseases, and immune-related conditions, said formula (I) being:

wherein
R represents a hydrogen atom, or phenyl optionally substituted by nitro, amino, alkylamino, acylamino, —NHC(S)NH-alkyl, sulfonylamido-alkyl,

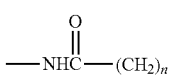

adamantane wherein n is an integer of from 1 to 20, —NH-adamantane;

X represents a hydrogen atom or OH;

Y represents

 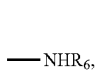 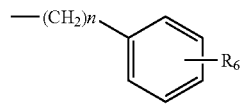

wherein n is an integer of from 0 to 6, and wherein $R_6$ represents a $C_{2-20}$ linear or branched alkyl or alkenyl chain which may be optionally substituted with hydroxyl,

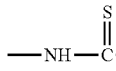 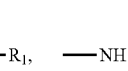
 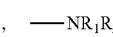

wherein $R_1$, $R_2$ and $R_3$, independently represent $C_1$-$C_6$ alkyl or $C_1$-$C_6$ alkenyl;

Z represents a hydrogen atom, —OH, a mono- or disaccharide, a monosaccharide sulfate, or choline phosphate; and W represents a hydrogen atom, or $C_{1-20}$ linear or branched alkyl or alkenyl chain which may be optionally substituted with hydroxyl, with the proviso that if R is hydrogen, Y is not

In a particular embodiment, the invention provides the use of a specific compound of formula (I), that may be a compound of formula (III):

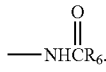

wherein

R represents a hydrogen atom, or phenyl optionally substituted by nitro, amino, alkylamino, acylamino, —NHC(S)NH-alkyl, sulfonylamido-alkyl,

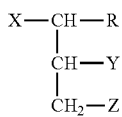

adamantane wherein n is an integer of from 1 to 20, —NH-adamantane, —NH-t-BOC, —NH-FMOC, or NH-CBZ;

X represents a hydrogen atom or the group —OH;

Y represents

wherein $R_6$ is a linear or branched alkyl or alkenyl chain which may be optionally substituted with hydroxyl,

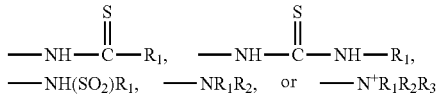

wherein $R_1$, $R_2$ and $R_3$ independently represent $C_1$-$C_8$ alkyl or $C_1$-$C_6$ alkenyl; and Z represents a hydrogen atom, —OH, a mono- or disaccharide, a monosaccharide sulfate, or choline phosphate, and pharmaceutically acceptable salts and isomers thereof, wherein the diseases are any one of neurodegenerative disease, metabolism associated disease, and immunity related disease.

BRIEF DESCRIPTION OF THE DRAWINGS

The above and other characteristics and advantages of the invention will be more readily apparent through the following examples, and with reference to the appended drawings, wherein.

Figure shows a graph demonstrating the survival of MDA-MB-435 cells in nude mice, after treatment with AD2750. Abbreviations: mic. (mice), tum. (tumor), dea. (dead), cont. (control).

Figure 2:
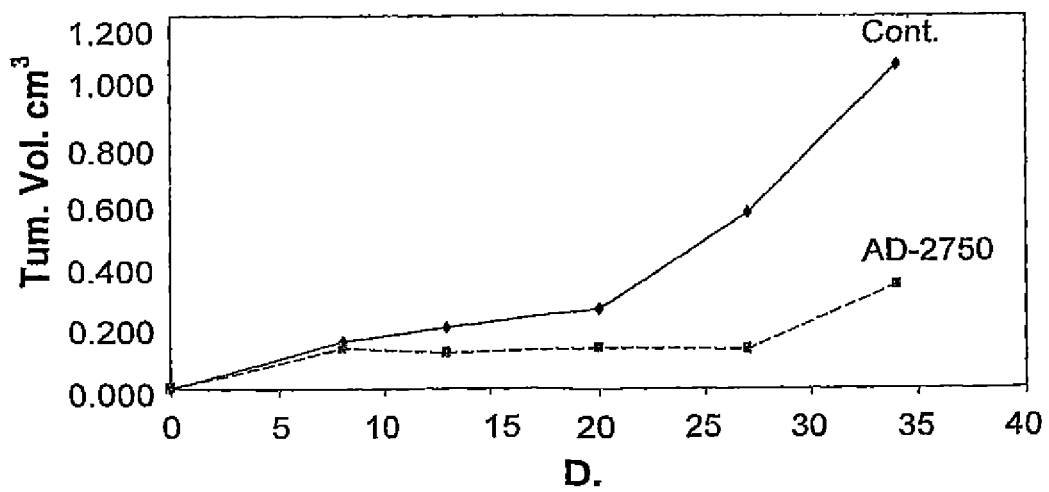

FIG. 2: Pancreas Tumor (CRL-1687) Growth in CD1-Nude Mice

Figure shows a graph demonstrating the growth of pancreas tumor in nude mice with/without the treatment with AD2750. Abbreviations: Tum. (tumor), Vol. (volume), cont. (control), D (days).

Figure 3A:
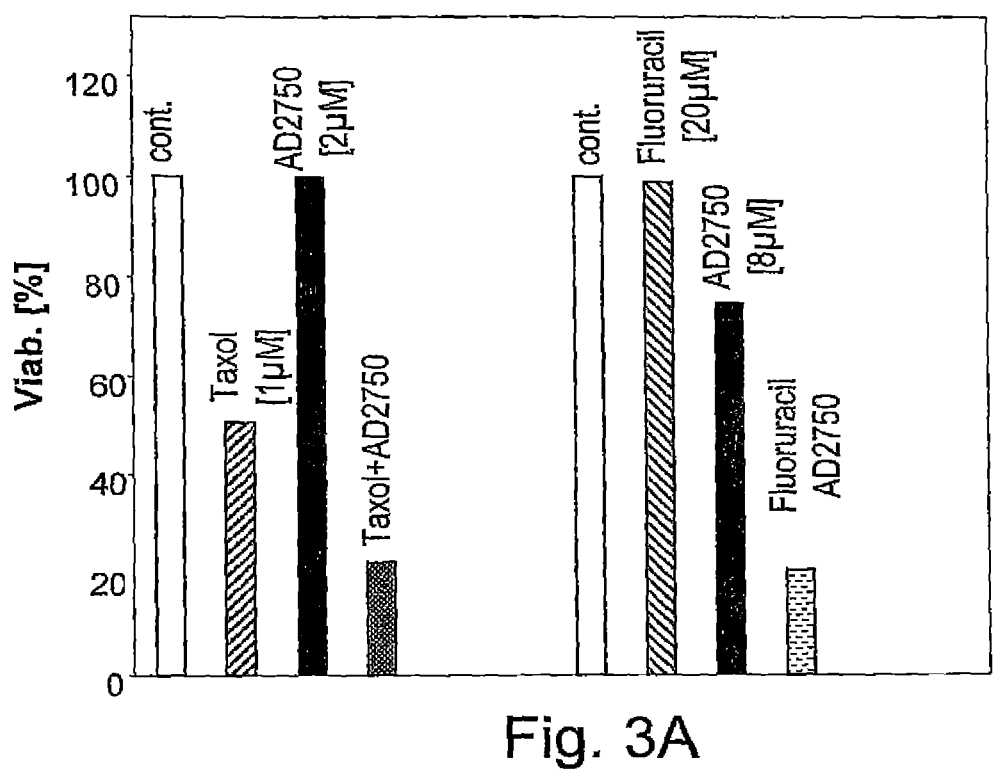
Figure 3B:
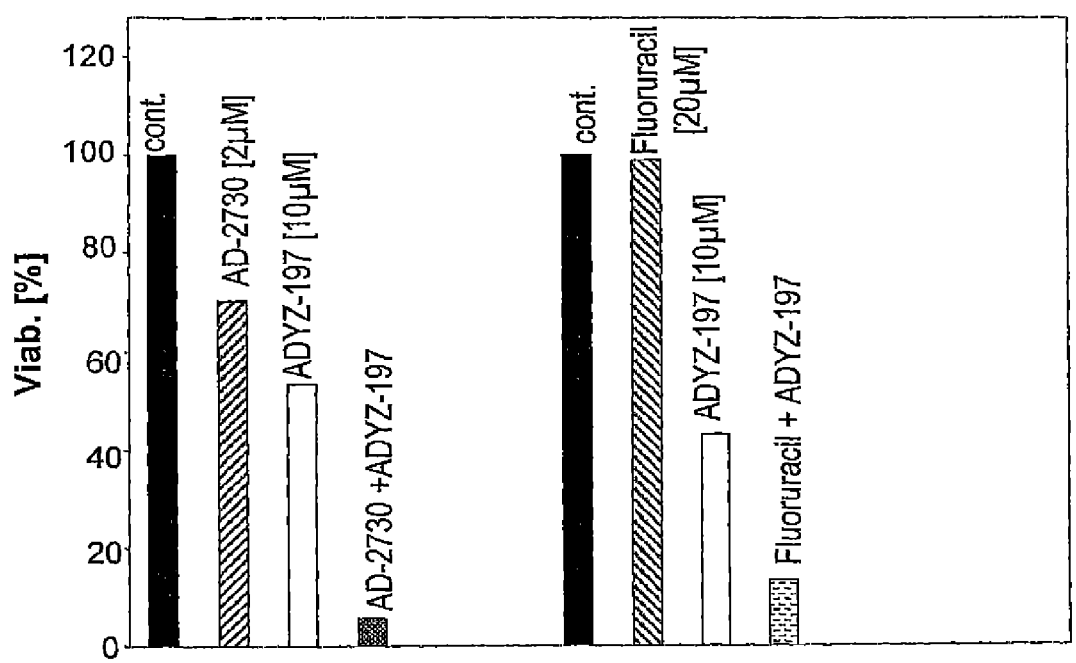

FIG. 3A-3B: The viability of pancreatic cells using different drug combination for 24 h (MTT test)

The Figure shows two graphs demonstrating the viability of pancreas tumor cells in culture during combined treatment of the compounds of the invention with known chemotherapeutic agents.

FIG. 3A: shows treatment with AD2750 alone or in combination with Taxol or with Fluorouracil.

FIG. 3B: shows treatment with ADYZ197 alone or in combination with AD2730 (2-(butylamino)-1-phenylpropane-1,3-diol) or with Fluorouracil. Abbreviations: cont. (control), viab. (viability).

Figure 4A:
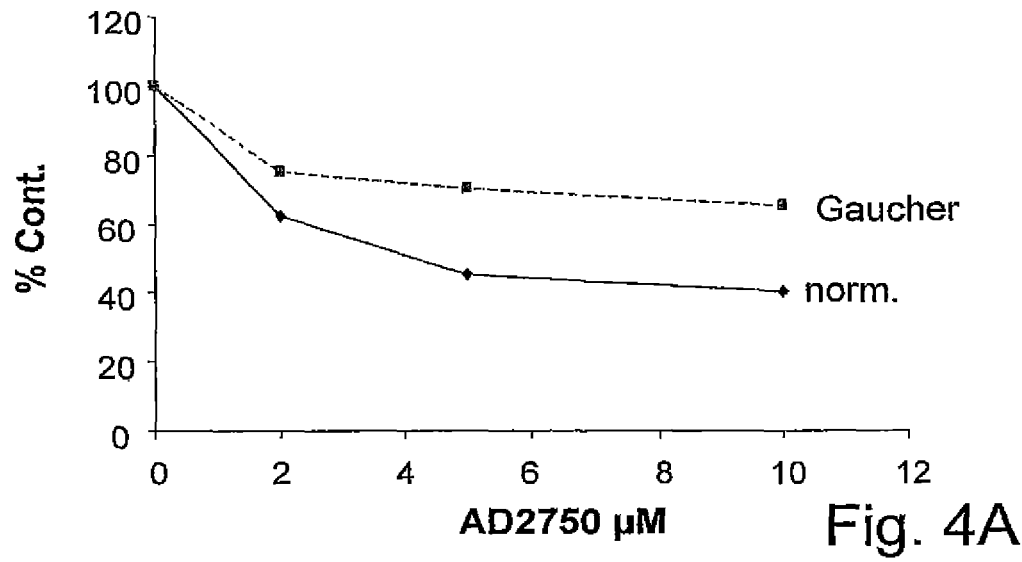
Figure 4B:
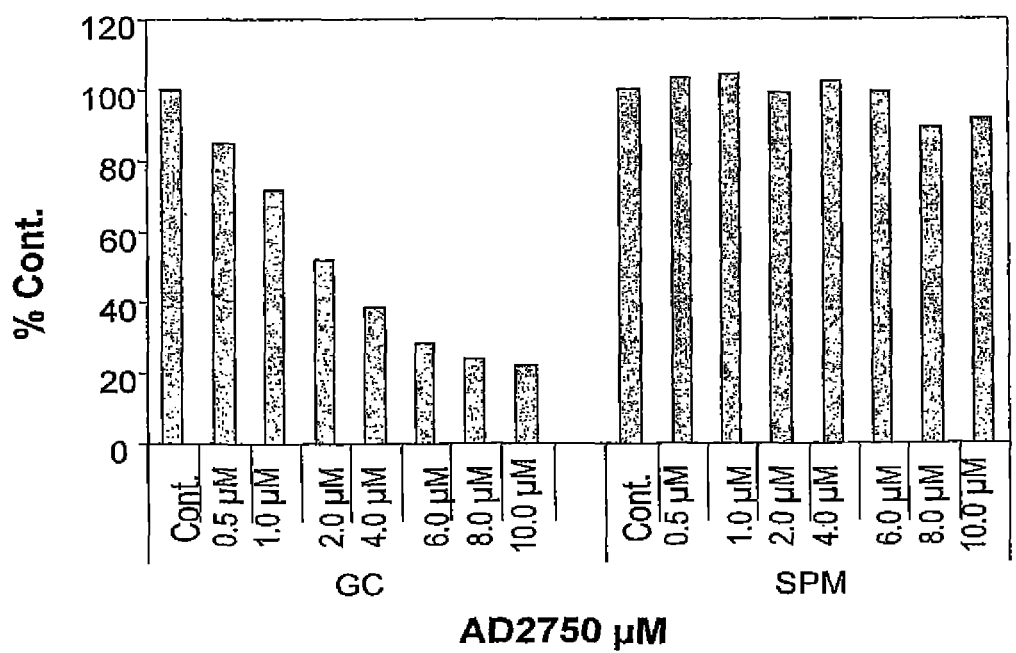

FIG. 4A-4B: Effect of AD-2750 on the synthesis of glucosylceramide and GC/SPM synthetases The Figure shows the effect of AD2750 on glucosylceramide/sphingomyelin synthesis in lymphoblasts.

FIG. 4A: shows the effect on the synthesis of glucosylceramide.

FIG. 4B: shows the effect on GC/SPM synthetases. Abbreviations: cont. (control), norm. (normal).

Figure 5:
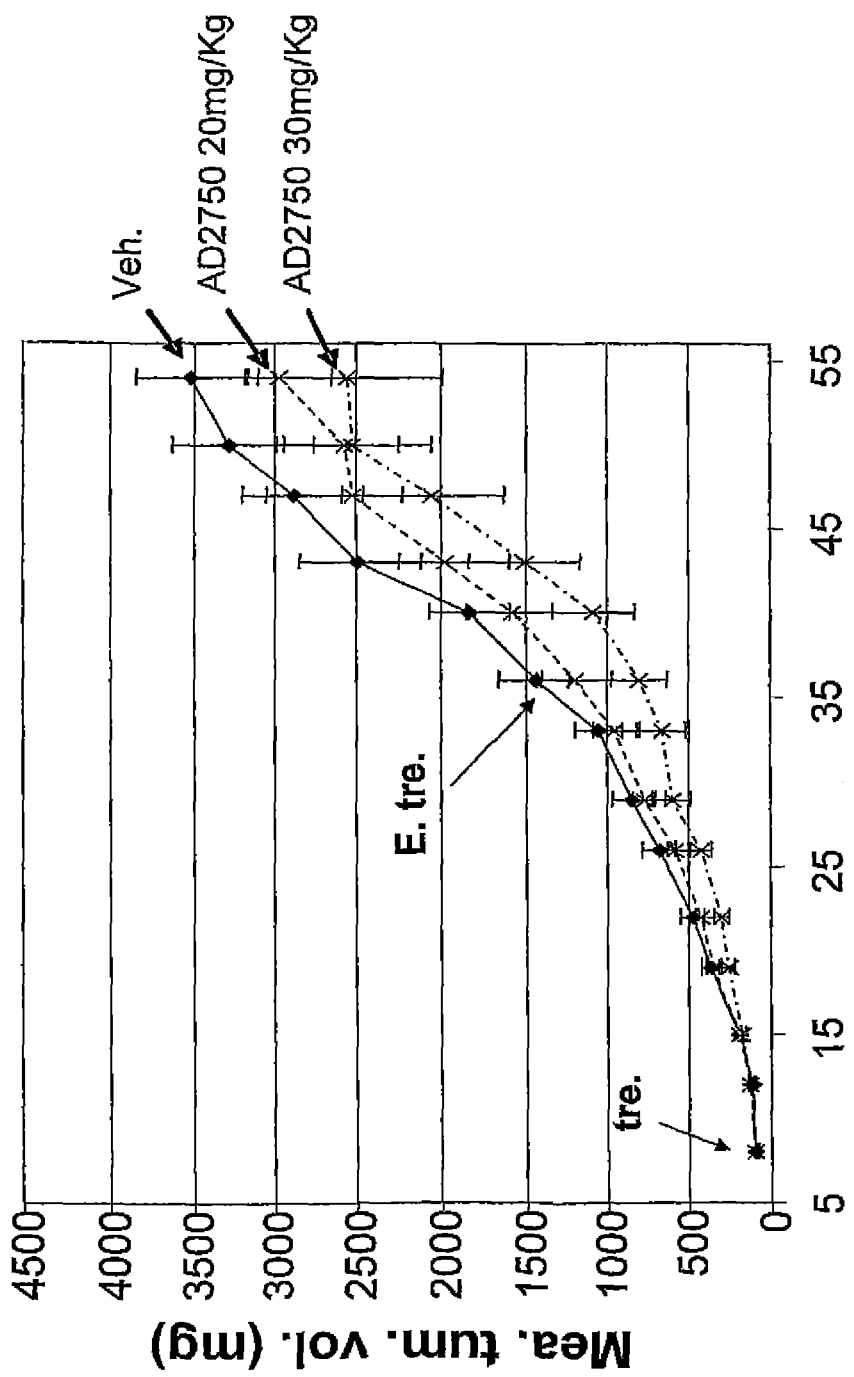

FIG. 5: In vivo efficacy study of AD2750 monotherapy treatment

Figure shows the in Vivo efficacy study results of treatment of nude mice (i.p) carrying a Pancreatic tumor [BxPC-3 cell line model], with two different concentrations of AD2750 (20 and 10 mg/kg), as compared to vehicle control treatment. Graph demonstrates mean tumor volume through the days of treatment. Abbreviations; Mea. (mean), tum. (tumor), vol. (volume), D (day), Veh. (vehicle), E. (end), tre. (treatment).

Figure 6:
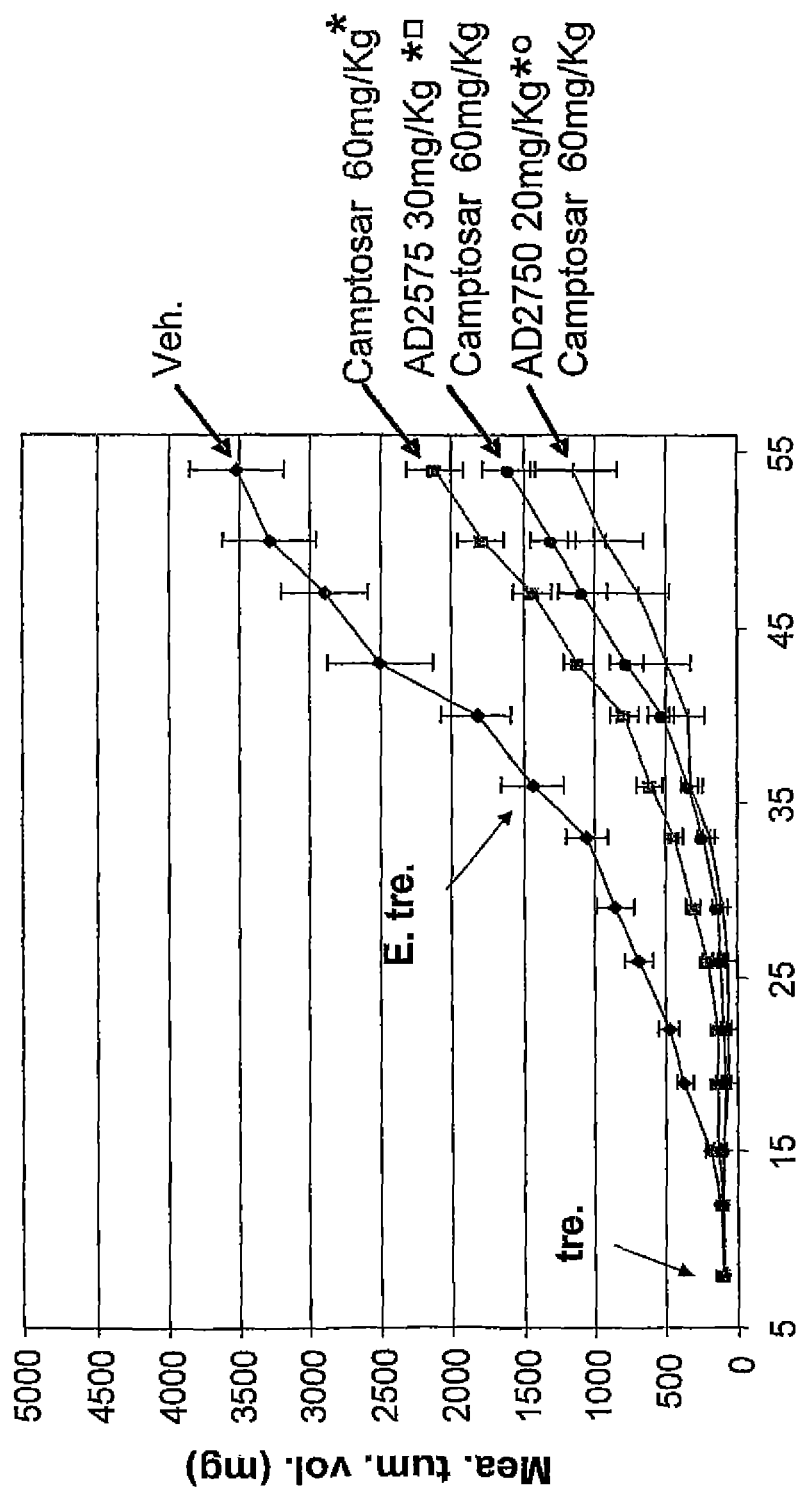

FIG. 6: In vivo efficacy study of AD2750 combined with Camptosar treatment

Figure shows the in vivo efficacy study results of treatment of nude mice (i.p) carrying a Pancreatic tumor [BxPC-3 cell line model], with two different concentrations of AD2750 (20 and 30 mg/kg) combined with Camptosar (60 mg/kg), as compared to vehicle control treatment. Graph demonstrates mean tumor volume through the days of treatment. * P-value vs. vehicle <0.05 from day 19-54, □ P-value vs. camptosar <0.05 from day 29-36 and o P-value vs. camptosar <0.05 from day 19-54.

Abbreviations: Mea. (mean), tuna. (tumor), vol. (volume), D (day), Veh. (vehicle), E. (end), tre. (treatment).

Figure 7:
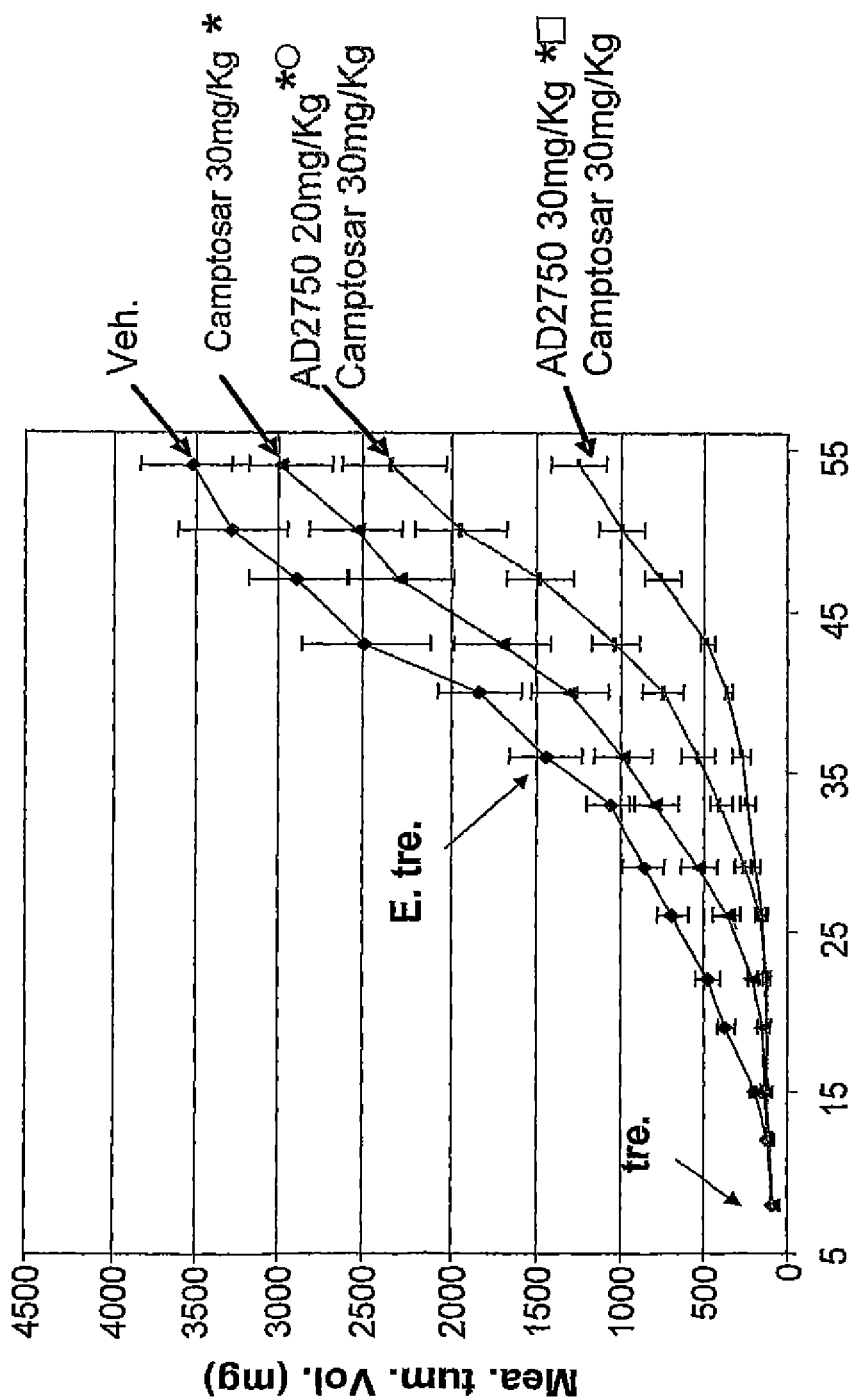

FIG. 7: In viva efficacy study of AD2750 combined with Camptosar treatment

Figure shows the in vivo efficacy study results of treatment of nude mice (i.p) carrying a Pancreatic tumor [BxPC-3 cell line model], with two different concentrations of AD2750 (20 and 30 mg/kg) combined with Camptosar (30 mg/kg), as compared to vehicle control treatment. Graph demonstrates mean tumor volume through the days of treatment. * P-value vs. vehicle <0.05 from day 19-54, □ P-value vs. camptosar <0.05 from day 26-33 and o P-value vs. camptosar <0.05 from day 26-54.

Abbreviations: Mea. (mean), tum. (tumor), vol. (volume), D (day), Veh. (vehicle), E. (end), tre. (treatment).

DETAILED DESCRIPTION OF THE INVENTION

New ceramide analogs of formula (I) have now been synthesized, and have exhibited powerful effects in inhibiting a number of cancerous cells. Said analogs are potent in killing a variety of cells, including drug-sensitive and thug-resistant cells, alone or in combination with other anti-cancer drugs. The pharmaceutical compositions comprising the analog of the invention are thus particularly intended for the treatment of cell proliferative diseases. Ceramide analogs of the invention are further useful for treating cystic fibrosis, Alzheimer disease, leishmaniasis, mycoplasma infections, bacterial infections, fungal infections, viral infections, allergy, diabetes, malaria, and lipid storage diseases (e.g. Gaucher, Nieman-Pick, and Tay-Sachs disease). The pharmaceutical compositions of the invention are further intended for the treatment of immuno-degenerative diseases, in particular GVHD (Graft Versus Host Disease).

Ceramide analogs of formula (I) are provided:

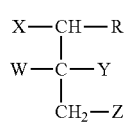

(I)

wherein

R represents a hydrogen atom, or phenyl optionally substituted by nitro, amino, alkylamino, acylamino, —NHC(S)NH-alkyl, sulfonylamido-alkyl,

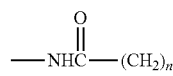

adamantine wherein n is an integer of from 1 to 20, —NH-adamantane;

X represents a hydrogen atom or OH;

Y represents

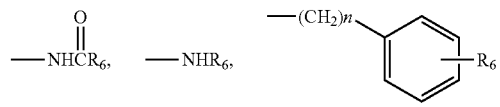

wherein n is an integer of from 0 to 6, and wherein $R_6$ represents a $C_{2-20}$ linear or branched alkyl or alkenyl chain which may be optionally substituted with hydroxyl,

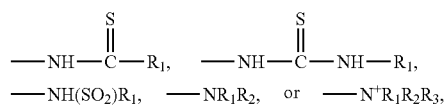

wherein $R_1$, $R_2$ and $R_3$, independently represent $C_1$-$C_6$ alkyl or $C_1$-$C_6$ alkenyl;

Z represents a hydrogen atom, —OH, a mono- or disaccharide, a monosaccharide sulfate, or choline phosphate; and W represents a hydrogen atom, or $C_{1-20}$ linear or branched alkyl or alkenyl chain which may be optionally substituted with hydroxyl, with the proviso that if R is hydrogen, Y is not

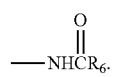

The ceramide analogs, as well as their isomers and pharmaceutically acceptable salts, are suitable for using in the preparation of medicaments for treating proliferative disorders, neurodegenerative disorders, metabolism-associated conditions, infectious diseases, and immunity-associated conditions.

The inventors have now discovered a specific novel group of the compounds of Formula I, being the compounds of Formula II.

Thus, according to a first aspect, the present invention relates to a compound of formula (II), the compound being

(II)

wherein

X represents a hydrogen atom or OH;

Y represents

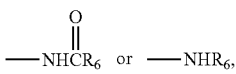

wherein $R_6$ represents a $C_{1-20}$ linear or branched alkyl or alkenyl chain which may be optionally substituted with hydroxyl; and W represents a hydrogen atom or $C_{1-20}$ linear or branched alkyl or alkenyl chain which may be optionally substituted with hydroxyl, or a pharmaceutically acceptable salt or isomer thereof.

According to one embodiment, the invention provides the compound of formula (II) wherein X represents OH.

In another embodiment, the compound of formula (II), wherein $R_6$ represents a $C_{10-18}$ or $C_{14-18}$ linear or branched alkyl.

Another embodiment relates to the compound of formula (II), wherein W represents a hydrogen atom.

The invention further provides the compound of formula (II), wherein W represents $CH_2OH$.

According to a specifically preferred embodiment, the compound of formula (II) may be selected from:

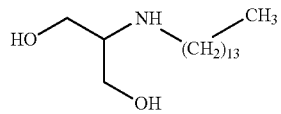

2-(tetradecylamino)propane-1,3-diol, also designated herein as AD2750;

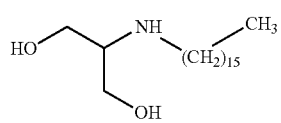

2-(hexadecylamino)propane-1,3-diol, also designated herein as ADYZ252;

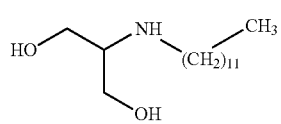

2-(dodecylamino)propane-1,3-diol, also designated herein as ADYZ74;

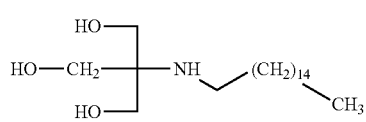

2-(hexadecylamino)-2-(hydroxymethyl)propane-1,3-diol, also designated herein as ADYZ243;

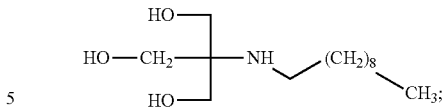

2-(decylamino)-2-(hydroxymethyl)propane-1,3-diol, also designated herein as ADYZ195;

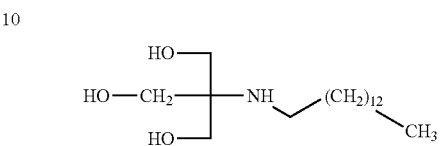

2-(tetradecylamino)-2-(hydroxymethyl)propane-1,3-diol, also designated herein ADYZ196; and

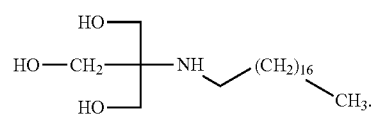

2-(octadecylamino)-2-(hydroxymethyl)propane-1,3-dial, also designated herein ADYZ197.

In one particular embodiment, the present invention relates to a compound of formula (I), the compound being

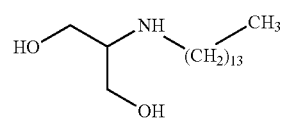

designated herein as AD2750. It should be noted that this compound is also referred to as BL 4060 or ADYZ157.

As shown by the following Examples, compound AD2750 turned out to have a remarkable potency for curing tumors in a mouse.

According to another aspect, the invention relates to a pharmaceutical composition comprising as active ingredient a compound of formula (II) wherein the substituents are as defined above, and optionally further comprising pharmaceutically acceptable carrier, adjuvant or diluent. In one particular embodiment, the present invention relates to a pharmaceutical composition comprising as an active ingredient a compound of formula (II), the said compound being AD2750.

According to one specific embodiment the pharmaceutical composition of the invention may further comprise at least one additional therapeutic agent.

In yet another preferred embodiment the pharmaceutical composition of the invention may be specifically applicable for the treatment of a pathological disorder selected from the group consisting of proliferative disorders, neurodegenerative disorders, metabolism-associated conditions, infectious diseases, and immune-related disorders.

More specifically, the invention relates to a composition comprising a compound of Formula II, for treating a cell proliferative, particularly cancerous, disease, specifically including killing of wild type and drug-resistant cancer cells, in a patient in need of such treatment. In one particular embodiment, the present invention relates to a composition for treating a cancerous disease, particularly for killing of wild type and drug-resistant cancer cells, in a patient in need of such treatment. According to this particular embodiment, the composition comprises therapeutically effective amount of said compound AD2750.

In another embodiment, a pharmaceutical Composition of the invention which comprises at least one compound of above formula (II) may used for the treatment of immunodegenerative disorders, particularly GVHD.

The compounds of the invention are generally provided in the form of pharmaceutical compositions. Said compositions are for use by injection or by oral uptake. The pharmaceutical compositions of the invention generally comprise a buffering agent, an agent which adjusts the osmolarity, and optionally, one or more carriers, excipients and/or additives as known in the art, e.g., for the purposes of adding flavors, colors, lubrication, or the like to the pharmaceutical composition.

Each carrier should be both pharmaceutically and physiologically acceptable in the sense of being compatible with the other ingredients and not injurious to the subject to be treated. While formulations include those suitable for rectal, nasal, preferred formulations are intended for oral or parenteral administration, including intramuscular, intradermal, subcutaneous and specifically intravenous administration. The formulations may conveniently be presented in unit dosage form and may be prepared by any methods known in the art of pharmacy. Said carriers may include starch and derivatives thereof, cellulose and derivatives thereof, e.g., microcrystalline cellulose, xanthan gum, and the like. Lubricants may include hydrogenated castor oil and the like.

As used herein "pharmaceutically acceptable carrier" includes any and all solvents, dispersion media, and coatings that are not harmful to the subject. Antibacterial and antifungal agents may be included. The use of such media and agents for pharmaceutical active substances is well known in the art.

The compositions of the invention may be administered in a variety of ways. By way of non-limiting example, the composition may be delivered by injection intravenously, intramuscularly, or intraperitoneally. Intravenous administration, for example, is advantageous. A preferred pharmaceutical formulation is preferably used for administration by injection, including intravenous injection.

The pharmaceutical forms suitable for injection include sterile aqueous solutions or dispersions and sterile powders for the extemporaneous preparation of sterile injectable solutions or dispersions. In all cases the form must be sterile and must be fluid to the extent that easy syringeability exists. It must be stable under the conditions of manufacture and storage and must be preserved against the contaminating action of microorganisms, such as bacteria and fungi. The carrier can be solvent or dispersion medium containing, for example, water, ethanol, polyol (for example, glycerol, propylene glycol, and liquid polyethylene glycol, and the like), suitable mixtures thereof, and vegetable oils. The proper consistency can be maintained, for example, by the use of a coating, such as lecithin, by the maintenance of the required particle size in the case of dispersion, and further by the use of surfactants.

Sterile injectable solutions are prepared by incorporating the active compounds in the required amount in the appropriate solvent with various of the other ingredients enumerated above, as required, followed by filter sterilization. Generally, dispersions are prepared by incorporating the various sterilized active ingredients into a sterile vehicle which contains the basic dispersion medium and the required other ingredients from those enumerated above.

In the case of sterile powders for the preparation of the sterile injectable solutions, the preferred method of preparation are vacuum-drying and freeze drying techniques which yield a powder of the active ingredient plus any additional desired ingredient from a previously sterile-filtered solution thereof.

The preparation of pharmaceutical compositions is well known in the art and has been described in many articles and textbooks, see e.g., Remington's Pharmaceutical Sciences, Gennaro A. R. ed., Mack Publishing Company, Easton, Pa., 1990, and especially pages 1521-1712 therein.

Additives may also be designed to enhance uptake of the active agent across cell membranes. Such agents are generally agents that will enhance cellular uptake of the molecules of the invention. For example, the compounds of the invention may be enclosed within liposomes. The preparation and use of liposomes, e.g., using particular transfection reagents, is well known in the art. Other methods of obtaining liposomes include the use of Sendai virus or of other viruses.

The dose of the active agent may vary. The dose would generally depend on the disease, the state of the disease, age, weight and sex of the patient, and is to be determined by the attending physician.

As shown by the following Examples, the compounds of the invention demonstrate an anti-cancerous activity, when administered alone or even in combination with additional therapeutic agents. Therefore, according to another aspect, the invention provides a composition comprising a combination of at least one compound of formula (II) or a pharmaceutically acceptable salt or isomer thereof, and at least one additional therapeutic agent. The combined composition of the invention may optionally further comprise at least one pharmaceutically acceptable carrier, diluent, excipient and/or additive.

Disclosed herein is a therapeutic combination that contains at least one therapeutically active amount of a compound of Formula II, preferably, any of compounds AD2750, ADYZ197, ADYZ252, ADYZ74, ADYZ243 and ADYZ195, ADYZ196 as described by the invention, and optionally at least one additional therapeutic agent.

The present invention therefore particularly relates to safe, non-interfering, synergistic or additive compositions combining at least one compound of Formula II, preferably, such compound may be any of the compounds of the invention, specifically, AD2750 or ADYZ197, with at least one therapeutic agent, for example, topoisomerase inhibitors, nucleic acids antimetabolites, or antimitotic agents. Those synergistic combinations are useful in treating subjects suffering from a pathologic disorder such as proliferative disorders, neurodegenerative disorders, metabolism-associated conditions, infectious diseases, and immune-related disorders. The synergistic compositions of the invention may also be used for the treatment of subjects presenting symptoms or signs of such disorders.

A particular embodiment of such combined composition may comprise at least one of the compounds of Formula II described by the invention, preferably, the AD2750 compound, with at least one therapeutic agent, for example, topoisomerase inhibitors, nucleic, acids anti metabolites, and antimitotic agents. More specifically, any of the compounds of Formula II descried by the invention may be combined with a therapeutic agent such as irinotecan, taxol or fluorouracil.

A specific combination also exemplified by Example 11, may be AD2750 and a topoisomerase 1 inhibitor such as Irinotecan, which its hydrochloride form is known as Camptosar.

In yet another embodiment, the combined composition of the invention may comprise at least one compound of Formula II, specifically, AD2750 and a therapeutic agent such as Taxol.

Still further, the invention provides a combined composition comprising a compound of Formula II, specifically, AD2750 and a therapeutic agent such as fluorouracil.

In yet another embodiment, the invention provides a combined composition comprising at least two compounds of Formula II, for example, a combination of AD2730 and ADYZ197.

By synergic combination is meant that the effect of both therapeutic agent and any of the compounds of formula II of the invention is greater than the sum of the therapeutic effects of administration of any of these compounds separately, as a sole treatment.

It should be appreciated that the combined compounds of the present invention may be generally administered in the form of a pharmaceutical composition comprising either one or both compounds of this invention (any of the compounds of Formula II described by the invention or any combination thereof and a therapeutic agent) together with a pharmaceutically acceptable carrier or diluent. Thus, the compounds used by this invention can be administered either individually in a kit or together in any conventional oral or intraperitoneal dosage form.

More particularly, since the present invention relates to the treatment of diseases and conditions with a combination of active ingredients which may be administered separately, the invention also relates as a further aspect, to combining separate pharmaceutical compositions in kit form. The kit may includes two separate pharmaceutical compositions: the first composition may be at least one compound of Formula II, preferably such compound may be any of the compounds of the invention, specifically, the compounds designated AD2750, ADYZ197, ADYZ252, ADYZ74, ADYZ243 and ADYZ195, ADYZ196 or any combinations, mixtures and derivative thereof and a pharmaceutically acceptable carrier or diluent, optionally in a first unit dosage form. The second composition may be at least one therapeutic agent, preferably, any one of a topoisomerase inhibitor, nucleic acid anti-metabolite, and anti-mitotic agent and a pharmaceutically acceptable carrier or diluent, optionally in a second unit dosage form. The kit includes container means for containing both separate compositions, such as a divided bottle or a divided foil packet. However, the separate compositions may also be contained within a single, undivided container. Typically the kit includes directions for the administration of the separate components. The kit form is particularly advantageous when the separate components are preferably administered in different dosage forms (e.g., oral and intraperitoneal), are administered at different dosage intervals, or when titration of the individual components of the combination is desired by the prescribing physician. The kit of the invention may optionally further comprises means for administering the different active ingredients (the compounds of Formula II according to the invention and the therapeutic agent).

According to one embodiment, the kit of the invention is intended for achieving a therapeutic effect in a subject suffering from a pathologic disorder for example, any one of proliferative disorders, neurodegenerative disorders, metabolism-associated conditions, infectious diseases, and immune-related disorders. Achieving a therapeutic effect is meant for example, slowing or preventing the progression of the disease symptoms.

Still further, the invention provides a method of treatment of a pathologic disorder comprising the step of administering to a subject in need thereof a therapeutically effective amount of a first and a second unit dosage forms comprised in the kit according to the invention.

It should be appreciated that both components of the kit, any one of the compounds of Formula II, specifically, any of the compounds AD2750, ADYZ197, ADYZ252, ADYZ74, ADYZ243 and ADYZ195, ADYZ196 of the invention, in the first dosage form and the therapeutic agent in the second dosage form may be administered simultaneously.

Alternatively, said first compound or dosage form and said second compound or dosage form are administered sequentially in either order.

The term "therapeutically effective amount" as used for the compositions and kits of the invention is intended to mean that amount of a drug or pharmaceutical agent that will elicit the biological or medical response of a tissue, a system, animal or human that is being sought by a researcher, veterinarian, medical doctor or other clinician.

As exemplified by the results of Examples 5, 6 and 11, a daily dose of the active ingredients in a preferred compositions, a preferred combined compositions or kits of the invention may contain between about 0.1 mg/kg body weight to 500 mg/kg, preferably, between about 1 to 500, 5 to 400, 10 to 300, 20 to 200 mg/kg per day, of any of the compounds of Formula II according to the invention. According to a specific embodiment, the effective amount may be any one of 1, 5, 10, 20, 30, 40, 50, 60, 70, 80, 90, 100, 150, 180, 200, 250, 300, 350, 400, 450 and 500 mg, per day of any of the compounds of the invention, either alone as a sole treatment or in combination with an additional therapeutic agent. In case of combined composition, a preferred amount of the additional agent may be between about 0.1 to 200, preferably, 0.5 to 100 mg/kg per day of the therapeutic agent, preferably, a topoisomerase inhibitor such as Camptosar. In a particular embodiment, where the AD2750 compound is used, a preferred amount may be 10, 20, 30 60 or 100 mg/kg, per day and about 10 to 100 mg/kg of a topoisomerase inhibitor such as Camptosar, at a quantitative ratio that may range between about 1:0.1 to 1:1000. These effective amounts of the compounds of the invention and the therapeutic agents may be optionally comprised within a dosage unit form. Additionally, the administration of the combined composition or the kit according to the invention may be periodically, for example, the periodic administration may be effected twice daily, three time daily, or at least one daily for at least about one day to three months. The advantages of lower doses are evident to those of skill in the art. These include, inter glia, a lower risk of side effects, especially in long-term use, and a lower risk of the patients becoming desensitized to the treatment.

In another embodiment, treatment using the combined compositions or kits of the invention may be effected following at least 1, 2, 3, 4, 5, 6, 7, 8, 9, 10, 14, 30, 60, 90 days of treatment.

It should be noted that the treatment of different conditions may indicate the use of different doses or different time periods these will be evident to the skilled medical practitioner.

According to another aspect, the invention relates to a method for the treatment of a subject suffering from a pathological disorder comprising the step of administering to said subject a therapeutically effective amount of the compound of Formula II, or any composition, combined composition or kit thereof, said disorder being any one of a proliferative disorder, a neurodegenerative disorder, metabolism-associated condition, infectious diseases, and an immune-related disorder.

In one specific embodiment, the invention relates to a method of treating a cell proliferative, particularly cancerous, disease, specifically including killing of wild type and drug-resistant cancer cells, in a patient in need of such treatment, comprising administering to said patient a therapeutically effective amount of a compound of formula (II) or of a pharmaceutical composition comprising the same, a combined composition or any kit thereof.

In one particular embodiment, the present invention relates to a method of treating a cancerous disease, particularly for killing of wild type and drug-resistant cancer cells, in a patient in need of such treatment comprising administering to said patient a therapeutically effective amount of said compound AD2750.

It should be appreciated that any of the compounds, compositions, combined compositions and kits of the invention may be applicable in the method of the invention.

According to one embodiment, administration step according to any of the methods of the invention may comprises oral, intravenous, intramuscular, subcutaneous, intraperitoneal, parenteral, transdermal, intravaginal, intranasal, mucosal, sublingual, topical, rectal or subcutaneous administration, or any combination thereof.

It should be further noted that for the method of treatment and prevention provided in the present invention, said therapeutic effective amount, or dosage, is dependent on severity and responsiveness of the disease state to be treated, with the course of treatment lasting from several days to several weeks, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. In general, dosage is calculated according to body weight, and may be given once or more daily, weekly, or monthly. Persons of ordinary skill in the art can easily estimate repetition rates for dosing based on measured residence times and concentrations of the combined composition of the invention in bodily fluids or tissues. Following successful treatment, it may be optional to have the patient undergo maintenance therapy to prevent the recurrence of the disease state, wherein the combined composition of the invention is administered in maintenance doses, once or more daily.

Moreover, different combinations of different ratios at different concentrations of at least one of the compounds of Formula II by the invention, particularly, the AD2750 compounds, and at least one therapeutic agent such as topoisomerase inhibitors, nucleic acids anti metabolites, and antimitotic agents, may be used for different disorders. It should be appreciated that any quantitative ratio may be used, for example: 1:1000, 1:2, 1:50, 1:200, 1:350, 1:500 and any possible combination.

As demonstrated by Example 11, treatment with any of the compositions, combined compositions or kits of the invention may increase survival of the treated subjects by at least 10%, at least 15%, at least 20%, at least 25%, at least 30%, at least 40%, at least 50%, at least 60%, at least 70%, at least 80% or even by at least 90% or 100% as compared to the survival of untreated subjects.

In general, the compounds, composition as well as the methods of the present invention may be used in the treatment of any autoimmune disease such as for example, but not limited to, GVHD, Eaton-Lambert syndrome, Goodpasture's syndrome, Greave's disease, Guillain-Barre syndrome, autoimmune hemolytic anemia (AIHA), hepatitis, insulin-dependent diabetes mellitus (IDDM), systemic lupus erythematosus (SLE), multiple sclerosis (MS), myasthenia gravis, plexus disorders e.g. acute brachial neuritis, polyglandular deficiency syndrome, primary biliary cirrhosis, rheumatoid arthritis, scleroderma, thrombocytopenia, thyroiditis e.g. Hashimoto's disease, Sjogren's syndrome, allergic purpura, psoriasis, mixed connective tissue disease, polymyositis, dermatomyositis, vasculitis, polyarteritis nodosa, polymyalgia rheumatica, Wegener's granulomatosis, Reiter's syndrome, Behget's syndrome, ankylosing spondylitis, pemphigus, bullous pemphigoid, dermatitis herpetiformis, insulin dependent diabetes, inflammatory bowel disease, ulcerative colitis and Crohn's disease.

As used herein to describe the present invention, the terms "malignant proliferative disorder", "cancer", "tumor" and "malignancy" all relate equivalently to a hyperplasia of a tissue or organ. If the tissue is a part of the lymphatic or immune systems, malignant cells may include non-solid tumors of circulating cells. Malignancies of other tissues or organs may produce solid tumors. In general, the compounds, composition, kits as well as the methods of the present invention may be used in the treatment of non-solid and solid tumors, for example, carcinoma, melanoma, leukemia, and lymphoma.

Therefore, according to a preferred embodiment, the compounds of Formula II of the invention or a composition, combinations or kits comprising the same, can be used for the treatment or inhibition of non-solid cancers, e.g. hematopoietic malignancies such as all types of leukemia, e.g. acute lymphocytic leukemia (ALL), acute myelogenous leukemia (AML), chronic lymphocytic leukemia (CLL), chronic myelogenous leukemia (CML), myelodysplastic syndrome (MDS), mast cell leukemia, hairy cell leukemia, Hodgkin's disease, non-Hodgkin's lymphomas, Burkitt's lymphoma and multiple myeloma, as well as for the treatment or inhibition of solid tumors such as tumors in lip and oral cavity, pharynx, larynx, paranasal sinuses, major salivary glands, thyroid gland, esophagus, stomach, small intestine, colon, colorecturn, anal canal, liver, gallbladder, extraliepatic bile ducts, ampulla of Vater, exocrine pancreas, lung, pleural mesothelioma, bone, soft tissue sarcoma, carcinoma and malignant melanoma of the skin, breast, vulva, vagina, cervix uteri, corpus uteri, ovary, fallopian tube, gestational trophoblastic tumors, penis, prostate, testis, kidney, renal pelvis, ureter, urinary bladder, urethra, carcinoma of the eyelid, carcinoma of the conjunctiva, malignant melanoma of the conjunctiva, malignant melanoma of the uvea, retinoblastoma, carcinoma of the lacrimal gland, sarcoma of the orbit, brain, spinal cord, vascular system, hemangiosarcoma and Kaposi's sarcoma.

According to another embodiment, the invention relates to a method for the treatment of a pathologic disorder, specifically, an infectious disease caused by a pathogenic agent. Pathogenic agents include prokaryotic microorganisms, lower eukaryotic microorganisms, complex eukaryotic organisms, viruses, fungi, prions, parasites, yeasts, toxins and venoms.

A prokaryotic microorganism includes bacteria such as Gram positive, Gram negative and Gram variable bacteria and intracellular bacteria. Examples of bacteria contemplated herein include the species of the genera *Treponema* sp., *Borrelia* sp., *Neisseria* sp., *Legionella* sp., *Bordetella* sp., *Escherichia* sp., *Salmonella* sp., *Shigella* sp., *Klebsiella* sp., *Yersinia* sp., *Vibrio* sp., *Hemophilus* sp., *Rickettsia* sp., *Chlamydia* sp., *Mycoplasma* sp., *Staphylococcus* sp., *Streptococcus* sp., *Bacillus* sp., *Clostridium* sp., *Corynebacterium* sp., *Proprionibacterium* sp., *Mycobacterium* sp., *Ureaplasma* sp. and *Listeria* sp.

Particular species include *Treponema pallidum, Borrelia burgdorferi, Neisseria gonorrhea, Neisseria meningitidis, Legionella pneumophila, Bordetella pertussis, Escherichia coli, Salmonella typhi, Salmonella typhimurium, Shigella dysenteriae, Klebsiella pneumoniae, Yersinia pestis, Vibrio cholerae, Hemophilus influenzae, Rickettsia rickettsii,*

*Chlamydia trachomatis, Mycoplasma pneumoniae, Staphylococcus aureus, Streptococcus pneumoniae, Streptococcus pyogenes, Bacillus anthracis, Clostridium botulinum, Clostridium tetani, Clostridium perfringens, Corynebacterium diphtheriae, Proprionibacterium acnes, Mycobacterium tuberculosis, Mycobacterium leprae* and *Listeria monocytogenes*.

A lower eukaryotic organism includes a yeast or fungus such as but not limited to *Pneumocystis carinii, Candida albicans, Aspergillus, Histoplasma capsulatum, Blastomyces dermatitidis, Cryptococcus neoformans, Trichophyton* and *Microsporum*.

A complex eukaryotic organism includes worms, insects, arachnids, nematodes, aemobe, *Entamoeba histolytica, Giardia larnblia, Trichomonas vaginalis, Trypanosoma brucei gambiense, Trypanosoma cruzi, Balantidium coli, Toxoplasma gondii, Cryptosporidium* or *Leishmania*.

The term "viruses" is used in its broadest sense to include viruses of the families adenoviruses, papovaviruses, herpesviruses: simplex, varicella-zoster, Epstein-Barr, CMV, pox viruses: smallpox, vaccinia, hepatitis B, rhinoviruses, hepatitis A, poliovirus, rubella virus, hepatitis C, arboviruses, rabies virus, influenza viruses A and B, measles virus, mumps virus, HIV, HTLV I and II.

The term "fungi" includes for example, fungi that cause diseases such as ringworm, histoplasmosis, blastomycosis, aspergillosis, cryptococcosis, sporotrichosis, coccidioidomycosis, paracoccidio-idoinycosis, and candidiasis.

The term parasite includes, but not limited to, infections caused by somatic tapeworms, blood flukes, tissue roundworms, ameba, and *Plasmodium, Trypanosoma, Leishmania,* and *Toxoplasma* species.

The invention further provides the use of a compound of formula (I), or a salt or isomer thereof, is the preparation of a medicament for treating a pathologic disorder selected from the group consisting of proliferative disorders, neurodegenerative disorders, metabolism-associated conditions, infectious diseases, and immune-related conditions, said formula (I) being:

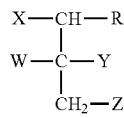
(I)

wherein

R represents a hydrogen atom, or phenyl optionally substituted by nitro, amino, alkylamino, acylamino, —NHC(S)NH-alkyl, sulfonylamido-alkyl,

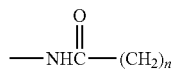

adamantane wherein n is an integer of from 1 to 20, —NH-adamantane;

X represents a hydrogen atom or OH;

Y represents

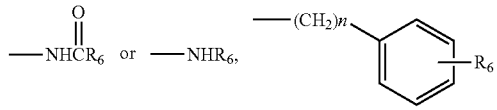

wherein n is an integer of from 0 to 6, and wherein $R_6$ represents a $C_{2-20}$ linear or branched alkyl or alkenyl chain which may be optionally substituted with hydroxyl,

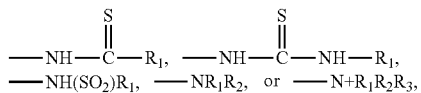

wherein $R_1$, $R_2$ and $R_3$, independently represent $C_1$-$C_6$ alkyl or $C_1$-$C_6$ alkenyl;

Z represents a hydrogen atom, —OH, a mono- or disaccharide, a monosaccharide sulfate, or choline phosphate; and W represents a hydrogen atom, or $C_{1-20}$ linear or branched alkyl or alkenyl chain which may be optionally substituted with hydroxyl, with the proviso that if R is hydrogen, Y is not

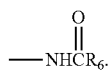

According to one embodiment, the use according to the invention may be wherein said compound of formula (I) is a compound of formula (III):

(III)

wherein

R represents a hydrogen atom, or phenyl optionally substituted by nitro, amino, alkylamino, acylamino, —NHC(S)NH-alkyl, sulfonylamido-alkyl,

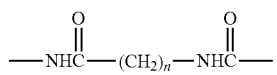

adamantane wherein n is an integer of from 1 to 20, —NH-adamantane, —NH-t-BOC, —NH-FMOC, or NH-CBZ;

X represents a hydrogen atom or the group —OH;

Y represents

wherein $R_6$ is a linear or branched alkyl or alkenyl chain which may be optionally substituted with hydroxyl,

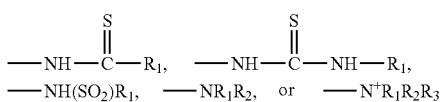

wherein $R_1$, $R_2$ and $R_3$ independently represent $C_1$-$C_6$ alkyl or $C_1$-$C_6$ alkenyl; and Z represents a hydrogen atom, —OH, a mono- or disaccharide, a monosaccharide sulfate, or choline phosphate, and pharmaceutically acceptable salts and isomers thereof, wherein the diseases are any one of neurodegenerative disease, metabolism associated disease, and immunity related disease.

According to one specific embodiment, the use of the invention may be for treating a neurodegenerative disorder such as Alzheimer's disease.

According to another embodiment, the use of the compounds of Formula I or III, ma be for treating metabolism-associated condition such a diabetes or cystic fibrosis.

In yet another embodiment, the use of the compounds of Formula I or III, according to the invention, may be for the treatment of an immune-related disorder such as GVHD or allergy.

It should be further appreciated that the present invention further encompasses combined compositions and kits comprising as an active ingredient any of the compounds of Formula I or III, with an additional therapeutic agent.

Disclosed and described, it is to be understood that this invention is not limited to the particular examples, methods steps, and compositions disclosed herein as such methods steps and compositions may vary somewhat. It is also to be understood that the terminology used herein is used for the purpose of describing particular embodiments only and not intended to be limiting since the scope of the present invention will be limited only by the appended claims and equivalents thereof.

It must be noted that, as used in this specification and the appended claims, the Singular forms "a", "an" and "the" include plural referents unless the content clearly dictates otherwise.

Throughout this specification and the Examples and claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The following examples are representative of techniques employed by the inventors in carrying out aspects of the present invention. It should be appreciated that while these techniques are exemplary of preferred embodiments for the practice of the invention, those of skill in the art, in light of the present disclosure, will recognize that numerous modifications can be made without departing from the spirit and intended scope of the invention.

EXAMPLES

Experimental Procedures

*Camptosar (supplied by Southern Research)
*Vehicle control contained 5% Cremophor EL/5% Ethanol/90% WFI.

BxPC-3 Human Pancreatic Tumor Model

Thirty-to-forty mg tumor fragments of BxPC-3 tumor from a continuous in vivo passage were implanted subcutaneously (sc) into athymic NCr-nu/nu mice using 12-gauge trocar needles.

Animals were purchased from NCI-approved animal facilities (4-5 weeks old) and acclimated in the laboratories one week prior to experimentation. The animals were housed in microisolator cages in a 12-hour light/dark cycle. Animals received filter-sterilized water and sterile rodent food ad libitum. Cages were changed a minimum of twice weekly. The animals were weighed twice weekly and observed daily (for about sixty days of experiment) for clinical signs.

Tumor Measurements and Body Weights: Tumors measurements and animal body weights are recorded twice weekly. Tumor volume was determined by caliper measurements (mm) and using the formula for an ellipsoid sphere:

$$\text{Length} \times \text{Wifth}^2/2 = \text{Volume}(\text{mm}^3)$$

This commonly used formula is also used to calculate tumor weight, assuming unit density (1 mm$^3$=1 mg).

Parameters Evaluated: For so tumors trials, a T-C value based on 1, 2, 3 or 4 tumor volume doubling time (days), as appropriate for the particular trial, was made. This evaluation is based on tumor size of the control animals at the end of the treatment period. A TIC (%) or TIC (%) value was determined. Statistical methods such as the Student's t-test or Mann-Whitney rank sum test were used to examine significant differences between various groups.

Example 1

Preparation of 2-(tetradecylamino)propane-1,3-diol (AD2750)

3 g of 2 amino-1,3-propanediol were dissolved in 100 ml ethanol, 4 ml tetradecyl bromide were added followed by 5 ml diisopropyl ethylamine. The mixture was heated to reflux for 24 hours in a 250 ml round bottom flask equipped with a reflux condenser and stirred on a magnetic stirrer. The solution was evaporated to dryness and dissolved in 200 ml dichloromethane:methanol, 2:1, transferred to a 500 ml separatory funnel and washed with 75 ml 0.2N HCl. Phases were separated and the organic phase was washed again with 75 ml 0.1N HCl and 15 ml methanol. The organic phase was separated and dried on 5 g magnesium sulfate, filtered and evaporated to dryness. The resulted oil was crystallized from ethanol: H$_2$O. Yield 1.2 g.

Example 2

Preparation of 2-(tetradecylamino)-2-(hydroxyinethyl)propane-1,8-diol (ADYZ196)

Two g of 2-amino-2-(hydroxymethyl)propane-1,3-diol hydrochloride were dissolved in 50 ml H$_2$O and 50 ml methanol in a round bottom flask. To the magnetically-stirred solution, 4 ml of tetra decyl aldehyde (tetradecanal) were added. The mixture was stirred for 30 min, after which 1.8 g of NaBH4 was added in several portions during 8 hours. The mixture was left to stir overnight, the solution was transferred to a separatory funnel, 50 ml of H$_2$O and 100 ml dichloromethane were added and the solvent mixture was shaken. The lower phase was collected, the aqueous-methanol phase was extracted twice with 50 ml 3:1 dichloromethane:methanol, the 3 lower phases were combined and shaken with 75 ml H₂O. The organic phase was dried with MgSO₄, filtered and evaporated to dryness. The residue was crystallized from ethanol:H₂O. Yield: 1.1 g.

Example 3

Preparation of 2-(octadecylamino)-2-(hydroxymethyl)propane-1,3-diol (ADYZ197)

Two g of 2-amino-2-(hydroxymethyl)propane-1,3-diol were reacted with 2 g octadecanoic acid (stearic acid) in 50 ml dichloromethane:methanol, 2:1, by addition of 1 g EDAC. The reaction mixture was stirred overnight, and then evaporated to dryness. The residue was dissolved in 4 ml dichloromethane-methanol, 1:1 and loaded onto a 50 cm×1.5 cm silica gel column prepared in dichloromethane. The compound was eluted with mixtures of dichloromethane and increasing amounts of methanol. Overall yield: 2.1 g.

2 g of the resulted N-[2-hydroxy-1,1-bis(hydroxymethyl) ethyl]octadecyl-amide were transferred to a three necks round bottom flask equipped with a dropping funnel, a cooling bath, and a magnetic stirrer. The compound was dissolved in 50 ml dry THF and the solution was cooled to 0° C. 40 ml of 1.0 M solution of $B_2H_6$ in THF (borane tetrahydrofuran complex) were added dropwise through the dropping funnel during 2 hours and then the mixture was left to react for another 2 hours at 0° C. The cooling bath was removed and the reaction was left to stir overnight. The next day, 10 ml of $H_2O$ were added slowly and the solution was evaporated to dryness, transferred to a separatory funnel, and 100 ml water, 100 ml dichloromethane and 50 ml methanol were added. Following shaking, the lower phase was collected and the upper, aqueous-methanolic phase was extracted twice with 50 ml $CH_2Cl_2$:MeOH, 3:1. The combined organic phases were washed with 100 ml $H_2O$, dried for 2 hours over MgSO₄, filtered and the solution was evaporated to dryness. The resulted product was crystallized from ethanol:H₂O. Yield: 0.9 g.

Example 4

Preparation of 2-(hexadecylamino)propane-1,3-diol (ADYZ252)

Two g of 2 amino-1,3-propanediol were reacted with 2 g hexadecanoic acid (palmitic acid) in 100 ml dichloromethane:methanol, 2:1, by addition of 1.5 g EDAC. The reaction mixture was stirred overnight, followed by evaporation to dryness. The residue was dissolved in 6 ml dichloromethane-methanol, 1:1 and loaded onto a 50 cm×1.5 cm silica gel column prepared in dichloromethane. The compound was eluted with mixtures of dichloromethane and increasing amounts of methanol. Overall yield: 1.8 g.

1.0 g. of the resulted 2-(hexadecanoylamino)propane-1,3-diol were transferred to a three necks round bottom flask equipped with a dropping funnel, a cooling bath, and a magnetic stirrer, under an air stream. The compound was dissolved in 200 ml dry THF and the solution wasp cooled to 0° C. 1.2 g of LiAlH₄ were added in small portions with strong stirring during 1 hour and then the mixture was left to react for another 2 hours at 0° C. The cooling bath was removed and the reaction was left to stir overnight. The next day, 2 ml of ethyl acetate followed by 10 ml of methanol and 10 ml of HCl 1N, were added very slowly and the solution was evaporated to approximately 20 ml. The mixture was transferred to a separatory funnel and 100 ml water, 100 ml dichloromethane and 50 ml methanol were added. Following shaking, the lower phase was collected and the upper, acidic-aqueous-methanolic phase was extracted twice with 50 ml $CH_2Cl_2$:MeOH, 3:1. The combined organic phases were washed with 100 ml HCl 0.1 N and then with 100 ml $H_2O$, dried for 2 hours over MgSO₄, filtered and evaporated to dryness. The resulted product was crystallized from ethanol:H₂O. Yield: 0.5 g.

Example 5

MDA-MB-435 Cells Survival in Nude Mice, after Treatment with AD2750

Figure 1:
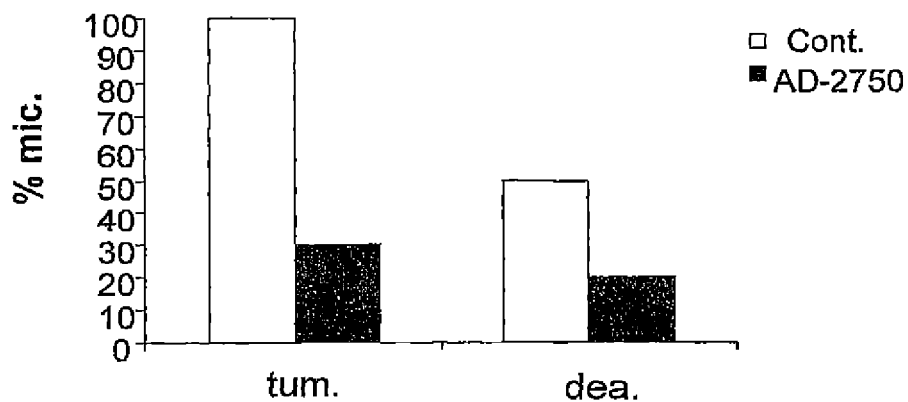
FIG. 1: MDA-MB-435 Survival Experiment

CD1-nude mice were injected iv with $3\times10^6$ MDA-MB-435 cells, which are usually considered as metastatic human breast cancer, but recently are also considered as model cells for melanoma. The mice were treated with AD2750, 20 mg/kg in the drinking water beginning day 1. On day 100, the remaining mice were sacrificed, and the pathology was determined. As clearly shown by FIG. 1, oral administration of AD2750, significantly reduced tumor incidence and increased survival of treated animals. Thus, these results demonstrate the feasibility of using the compound of the invention as an oral anti-cancerous drug, specifically, for breast carcinoma and melanoma applications.

Example 6

Pancreas Tumor Cell Growth in Nude Mice, after Treatment with AD2750

In order to examine the applicability of the compounds of the invention as an anti-cancerous drug, the inventors next examined the effect of i.p. administration of AD2750, on pancreas tumor. Therefore, CD1-nude mice were injected id with $5\times10^6$ pancreas tumor cells (CRL-1687). The mice were treated ip, with AD2750 beginning day 1, 30 mg/kg in 0.2 ml 10% CE, for up to 35 days. Tumor size was measured and calculated every 5-7 days beginning day 8. As shown in FIG. 2, i.p. administration of AD2750, results in reduction of about 5 folds in tumor volume.

Example 7

Pancreas Tumor Cell Viability after a Combined Treatment of AD2750 with Known Cytotoxic Drugs The inventors next examined the effect of combining the compound of the invention with known chemotherapeutic drugs. Pancreas tumor cells were incubated with 1 µM taxol and 2 µM AD2750 (separately and in combination). The results are shown in the left part of the graph, in FIG. 3A, as percent of viable cells (checked by MTT). A combination of 20 µM fluorouracil and 8 µM AD2750 is shown in the right part of the graph, in FIG. 3A. As shown by the figure, combination of AD2750 with known drugs as Taxol or Fluorouracil, markedly reduced tumor cell viability, illustrating the therapeutic potential of such combinations.

Example 8

Pancreas Tumor Cell Viability after a Combined Treatment of ADYZ197 with Fluorouracil and with AD2730 [2-(butylamino)-1-phenylpropane-1,3 diol]

The inventors next examined the potential anti-cancerous effect of other compounds of Formula II. Therefore, pancreas tumor cells were incubated with 2 µM AD2730 and 10 µM ADYZ197, separately and in combination. The results are presented in the left part of the graph, in FIG. 3B, as percent of viable cells (checked by MTT). Combination of both compounds of Formula resulted in a significant synergistic effect on reduction of cell viability. A combination of 20 μM fluorouracil and 10 μM ADYZ197, also resulted in a significant reduction of tumor cell viability, as shown in the right part of the graph, in FIG. 3B.

Example 9

AD2750 Affect on Glucosylceramide Synthesis in Lymphoblasts

The inventors next investigated the potential effect of the compounds of Formula II on metabolic disorders. Therefore, lymphoblasts, normal and from a Gaucher disease patient were incubated with increasing concentration of AD2750 for five min. Bodify-C3-ceramide was then added and incubation was continued for 3 hours. The cells where then extracted, and the fluorescence of the glucosylceramide and sphingomyelin spots was quantified by HPLC. The results are summarized in FIG. 4A.

Example 10

AD2750 Affect on Glucosylceramide/Sphingomyelin Synthesis in HL-60 Cells (being a Model for Acute Promyelocytic Leukemia)

HL60 were incubated with increasing concentration of AD2750 for 1 hour. Bodify-C3-ceramide was then added and incubation was continued for another 23 hours. The cells where then extracted, and the fluorescence of the glucosylceramide and sphingomyelin spots was quantified by HPLC. The results are summarized in FIG. 4B.

TABLE 1

| Analog | Line | Type | Incubation time (hours) | FCS | IC50 | No. of plated cells |
|---|---|---|---|---|---|---|
| AD2750 | Du-145 | Prostate | 24 | no | 3.3 uM | $0.1 \times 10^6$/ml |
| AD2750 | Du-145 | Prostate | 72 | yes | 7.5 uM | $0.05 \times 10^6$/ml |
| AD2750 | LNCaP | Prostate | 24 | no | 4.9 uM | $0.1 \times 10^6$/ml |
| AD2750 | LNCaP | Prostate | 24 | yes | 15.2 uM | $0.1 \times 10^6$/ml |
| AD2750 | LNCaP | Prostate | 48 | yes | 8.7 uM | $0.1 \times 10^6$/ml |
| AD2750 | LNCaP | Prostate | 72 | yes | 3.9 uM | $0.05 \times 10^6$/ml |
| AD2750 | PC-3 | Prostate | 24 | yes | 12.2 uM | $0.1 \times 10^6$/ml |
| AD2750 | PC-3 | Prostate | 72 | yes | 6.8 uM | $0.05 \times 10^6$/ml |
| AD2750 | CRL-5803 | NSCLC (Lung carcinoma) | 24 | yes | 11 uM | $0.1 \times 10^6$/ml |
| AD2750 | CRL-1687 | Pancreas | 24 | yes | 15 uM | $0.2*10^6$/ml |
| AD2750 | CRL-5891 | NSCLC (Lung carcinoma) | 24 | no | 8 uM | $0.1 \times 10^6$/ml |
| AD2750 | MEL624 | Melanoma | 24 | yes | 9 uM | $0.1 \times 10^6$/ml |
| AD2750 | CRL-1976 | Sarcoma | 24 | yes | 5 uM | $0.2*10^6$/ml |
| AD2750 | CCL-224 | Colon | 24 | no | 13 uM | $0.2*10^6$/ml |
| ADYZ158 | LNCaP | Prostate | 24 | no | >50 uM | $0.1 \times 10^6$/ml |
| ADYZ158 | PC-3 | Prostate | 24 | no | >50 uM | $0.1 \times 10^6$/ml |
| ADYZ158 | CRL-5803 | NSCLC (Lung carcinoma) | 24 | yes | 50 uM | $0.1 \times 10^6$/ml |
| ADYZ190 | Du-145 | Prostate | 24 | no | >50 uM | $0.1 \times 10^6$/ml |
| ADYZ190 | PC-3 | Prostate | 24 | no | >50 uM | $0.1 \times 10^6$/ml |
| ADYZ190 | HL-60 | Promyelocytic leukemia | 24 | no | >50 uM | $0.1 \times 10^6$/ml |
| ADYZ191 | Du-145 | Prostate | 24 | no | >50 uM | $0.1 \times 10^6$/ml |
| ADYZ191 | PC-3 | Prostate | 24 | no | >50 uM | $0.1 \times 10^6$/ml |
| ADYZ195 | Du-145 | Prostate | 24 | no | >50 uM | $0.1 \times 10^6$/ml |
| ADYZ195 | PC-3 | Prostate | 24 | no | >50 uM | $0.1 \times 10^6$/ml |
| ADYZ197 | Du-145 | Prostate | 24 | yes | 7.5 uM | $0.1 \times 10^6$/ml |
| ADYZ197 | LNCaP | Prostate | 24 | no | 42.9 uM | $0.1 \times 10^6$/ml |
| ADYZ197 | LNCaP | Prostate | 48 | yes | 23.9 uM | $0.1 \times 10^6$/ml |
| ADYZ197 | LNCaP | Prostate | 72 | yes | 3.0 uM | $0.05 \times 10^6$/ml |
| ADYZ197 | PC-3 | Prostate | 48 | yes | 8.2 uM | $0.1 \times 10^6$/ml |
| ADYZ197 | PC-3 | Prostate | 72 | yes | 4.4 uM | $0.05 \times 10^6$/ml |
| ADYZ197 | CRL-1687 | Pancreas | 24 | yes | 22 uM | $0.2*10^6$/ml |
| ADYZ197 | HL-60 | Promyelocytic leukemia | 24 | no | 15 uM | $0.2*10^6$/ml |
| ADYZ197 | CRL-5803 | NSCLC (Lung carcinoma) | 24 | yes | 20 uM | $0.1 \times 10^6$/ml |
| ADYZ197 | CRL-5891 | NSCLC (Lung carcinoma) | 24 | no | 10 uM | $0.1 \times 10^6$/ml |
| ADYZ197 | CRL-1976 | Sarcoma | 24 | yes | 20 uM | $0.2*10^6$/ml |
| ADYZ197 | MEL624 | Melanoma | 24 | yes | 3 uM | $0.1 \times 10^6$/ml |
| ADYZ197 | PC-3 | Prostate | 48 | yes | 8.2 uM | $0.1 \times 10^6$/ml |

Example 11

Combined Treatment of AD2750 and Camptosar—In Vivo Efficacy Studies

Encouraged by the anti-tumorigenic effect of the compounds of the invention as a sole therapy or in combination with known chemotherapeutic agents shown in vitro in cell culture and in vivo using the CRL-1687 pancreas tumor model, the inventors next performed a further in vivo efficacy study using the BxPC-3 human pancreatic tumor xenograft model. Therefore, nine groups of athymic NCr-nu/nu mice implanted subcutaneously (s.c.) with fragments of BxPC-3 tumor from a continuous in vivo passage, were daily treated (i.p.) with AD2750 (20 or 30 mg/kg), alone or in combination with Camptosar (60 or 30 mg/kg) for 28 days, as indicated in Table 2. Mean tumor volume were measured and calculated for fifty five days of the experiment, as indicated in Experimental procedures. As clearly shown by FIG. 5, treatment with AD2750 clearly reduced tumor volume in a dose dependent manner. Combination of AD2750 with Camptosar as shown in FIGS. 6 and 7, resulted in a significant reduction in tumor velum % and thus demonstrates the feasibility of using AD2750 as an anti-cancerous drug alone and in combination with Camptosar.

TABLE 2

| Group | Compound | Dose (mg/kg/inj.) | n | Injection Volume | Route |
|---|---|---|---|---|---|
| 1 | Vehicle | 0 | 10 | 10 mL/kg | i.p. |
| 2 | Camptosar | 60 | 10 | 10 mL/kg | i.p. |
| 3 | Camptosar | 30 | 10 | 10 mL/kg | i.p. |
| 4 | AD2750 | 30 | 10 | 10 mL/kg | i.p. |
| 5 | AD2750 | 20 | 10 | 10 mL/kg | i.p. |
| 6 | AD2750 | 30 | 10 | 10 mL/kg | i.p. |
|   | Camptosar | 60 |   | 10 mL/kg | i.p. |
| 7 | AD2750 | 20 | 10 | 10 mL/kg | i.p. |
|   | Camptosar | 60 |   | 10 mL/kg | i.p. |
| 8 | AD2750 | 30 | 10 | 10 mL/kg | i.p. |
|   | Camptosar | 30 |   | 10 mL/kg | i.p. |
| 9 | AD2750 | 20 | 10 | 10 mL/kg | i.p. |
|   | Camptosar | 30 |   | 10 mL/kg | i.p. |

While this invention has been described in terms of some specific examples, many modifications and variations are possible. It is therefore understood that within the scope of the appended claims, the invention may be realized otherwise than as specifically described.

The invention claimed is:

1. A method for the treatment of a subject suffering from cancer, the method comprising the step of administering to said subject a therapeutically effective amount of the compound of Formula 11, or a pharmaceutically acceptable salt thereof or any composition comprising same:

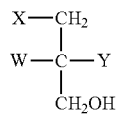

(II)

wherein

X represents OH;

Y represents

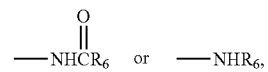

wherein $R_6$ represents a $C_{2-20}$ linear or branched alkyl or alkenyl chain which may be optionally substituted with hydroxyl; and W represents $C_{1-20}$ linear or branched alkyl or alkenyl chain substituted with hydroxyl, wherein said cancer is selected from colon cancer, pancreatic cancer, prostate cancer, leukemia, lung cancer, sarcoma and melanoma.

2. A method for the treatment of cancer, the method comprising administering to a subject a therapeutically effective amount of compound of follnula (I):

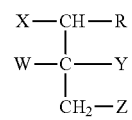

(I)

wherein

R represents a hydrogen atom, or phenyl optionally substituted by nitro, amino, alkylamino, acylamino, —NHC(S)NH-alkyl, sulfonylamido-alkyl,

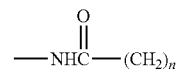

adamantane wherein n is an integer of from 1 to 20, or —NH-adamantane;

X represents OH;

Y represents

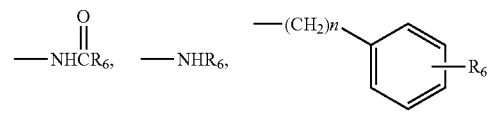

wherein n is an integer of from 0 to 6, and wherein $R_6$ represents a $C_{2-20}$ linear or branched alkyl or alkenyl chain which may be optionally substituted with hydroxyl,

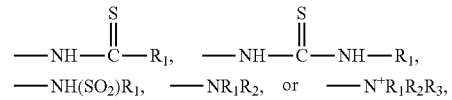

wherein $R_1$, $R_2$ and $R_3$, independently represent $C_1$-$C_6$ alkyl or $C_i$-$C_6$ alkenyl;

Z represents —OH; and

W represents $C_{1-20}$ linear or branched alkyl or alkenyl chain substituted with hydroxyl, with the proviso that if R is hydrogen, Y is not

wherein said cancer is selected from colon cancer, pancreatic cancer, prostate cancer, leukemia, lung cancer, sarcoma and melanoma.

3. The method of claim 1, wherein the compound of Formula (II) is

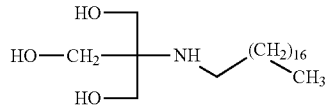

2-(octadecylamino)-2-(hydroxymethyl)propane-1,3-diol, also designated herein ADYZ197.

4. The method of claim 1, wherein the compound of Formula II is

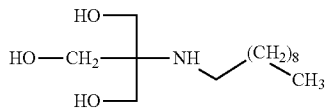

2-(decylamino)-2-(hydroxymethyl)propane-1,3-diol, also designated herein as ADYZ195.

\* \* \* \* \*

UNITED STATES PATENT AND TRADEMARK OFFICE
CERTIFICATE OF CORRECTION

PATENT NO.         : 9,340,488 B2                                        Page 1 of 1
APPLICATION NO.    : 14/540621
DATED              : May 17, 2016
INVENTOR(S)        : Arie Dagan et al.

It is certified that error appears in the above-identified patent and that said Letters Patent is hereby corrected as shown below:

Claims

Column 27, Claim 1, line 55, please amend "Formula 11" to --Formula II--;
Column 28, Claim 2, line 19, please amend "follnula (I):" to --formula (I):--;
Column 28, Claim 2, line 64, please amend "or $C_1$-$C_6$ alkenyl;" to --or $C_1$-$C_6$ alkenyl;--.

Signed and Sealed this
Twenty-third Day of August, 2016

Michelle K. Lee
*Director of the United States Patent and Trademark Office*